(12) United States Patent
Hibino et al.

(10) Patent No.: US 6,818,214 B2
(45) Date of Patent: Nov. 16, 2004

(54) TWO NOVEL GENES FROM PSORIATIC EPIDERMIS: PSORIASTATIN TYPE I AND PSORIASTATIN TYPE II

(75) Inventors: Toshihiko Hibino, Yokohama (JP); Tadahito Takahashi, Yokohama (JP); Peter C. Baciu, Rowley, MA (US); Paul F. Goetinck, Boston, MA (US)

(73) Assignees: The General Hospital Corporation, Boston, MA (US); Shiseido Co., Ltd., Tokyo (JP)

( * ) Notice: Subject to any disclaimer, the term of this patent is extended or adjusted under 35 U.S.C. 154(b) by 0 days.

(21) Appl. No.: 08/731,566

(22) Filed: Oct. 16, 1996

(65) Prior Publication Data

US 2003/0072752 A1 Apr. 17, 2003

Related U.S. Application Data

(60) Provisional application No. 60/013,755, filed on Mar. 20, 1996, and provisional application No. 60/005,679, filed on Oct. 17, 1995.

(51) Int. Cl.$^7$ ............................................. A61K 39/40
(52) U.S. Cl. .................................. 424/139.1; 424/152.1
(58) Field of Search ......................... 435/7.1; 436/503; 424/152.1, 139.1

(56) References Cited

PUBLICATIONS

Skolnick et al. TIBTECH, Jan. 2000. vol. 18, pp. 34–39, 2000.*
Ngo. et al. The Protein Folding Problem and Tertiary Structure Prediction, 1994, pp. 433, 492 & 495, 1994.*
Mery et al. Birkhauser, Boston, MA.*
Huang et al. Pharmacology and Therapeutics vol. 86 pp. 201–215, 2000.*
Takahashi et al., J. Invest. Derm., vol. 101:431, 1993, Sep. 1993.*
Tewari et al., J. Bio. Chem., vol. 270:3255–3260, 1995, Feb. 1995.*
Bianchi et al., J. Invest. Derm., vol. 103:829–833, 1994, Dec. 1994.*
Lerner, Nature, vol. 299: 592–596, 1982, Oct. 1982.*
Hibino, "Cloning of Psoriastatin, A Cathespin L–Specific Inhibitor, from Psoriatic Epidermis", Mol. Biology of the Cell 6:345a (1995) Abstract 2007.
Takahashi, "Structure and Inhibitory Effect of Psoriatic Tissue–Derived Cathespin L–Specific Inhibitor (Psoriastatin)" Mol. Biology of the Cell 5:367a (1994) Abs. 2132.
Hibino, "Cloning of Two Distinct Types of Psoriastatin cDNAs From Psoriatic Epidermis" J. of Invest. Dermatology 106(4):874 (1996) Abstract 414.
Takahashi, "Cathespin L–Specific High Molecular Weight Cystein Proteinase Inibitor (Psoriastatin) from Psoriatic Scales" J. Invest. Dermatology 101(3):431 Abs. 261.
Schneider, S.S. et al., A serine proteinase inhibitor locus at 18q21.3 contains a tandem duplication of the human squamous cell carcinoma antigen gene. *Proc. Natl. Acad. Sci. USA* 92:3147–3151 (1995).

* cited by examiner

*Primary Examiner*—Patrick J. Nolan
(74) *Attorney, Agent, or Firm*—Fish & Richardson P.C.

(57) ABSTRACT

A method of modulating cell proliferation or apoptosis comprising modulating psoriastatin activity.

9 Claims, 6 Drawing Sheets

Psoriastatin type-I DNA sequence

```
ATGAATTCACTCAGTGAAGCCAACACCAAGTTCATGTTCGACCTGTTCCAACAG
TTCAGAAAATCAAAAGAGAACAACATCTTCTATTCCCCTATCAGCATCACATCA
GCATTAGGGATGGTCCTCTTAGGAGCCAAAGACAACACTGCACAACAGATTAAG
AAGGTTCTTCACTTTGATCAAGTCACAGAGAACACCACAGGAAAAGCTGCAACA
TATCATGTTGATAGGTCAGGAGATGTTCATCACCAGTTTCAAAAGCTTCTGACT
GAATTCAACAAATCCACTGATGCATATGAGCTGAAGATCGCCAACAAGCTCTTC
GGAGAAAAACGTATCTATTTTTACAGGAATATTTAGATGCCATCAAGAAATTT
TACCAGACCAGTGTGGAATCTGTTGATTTTGCAAATGCTCCAGAAGAAAGTCGA
AAGAAGATTAACTCCTGGGTGGAAAGTCAAACGAATGAAAAAATTAAAAACCTA
ATTCCTGAAGGTAATATTGGCAGCAATACCACATTGGTTCTTGTGAACGCAATC
TATTTCAAAGGGCAGTGGGAGAAGAAATTTAATAAAGAAGATACTAAAGAGGAA
AAATTTTGGCCAAACAAGAATACATACAAGTCCATACAGATGATGAGGCAATAC
ACATCTTTTCATTTTGCCTCGCTGGAGGATGTACAGGCCAAGGTCCTGGAAATA
CCATACAAAGGCAAAGATCTAAGCATGATTGTGTTGCTGCCAAATGAAATCGAT
GGTCTCCAGAGGCTTGAAGAGGAACTCACTGCTGAGAAATTGATGGAATGGACA
AGTTTGCAGAATATGAGAGAGACACGTGTCGATTTACACTTACCTCGGTTCAAA
GTGGAAGAGAGCTATGACCTCAAGGACACGTTGAGAACCATGGGAATGGTGGAT
ATCTTCAATGGGGATGCAGACCTCTCAGGCATGACCGGGAGCCGCGGTCTCGTG
CTATCTGGAGTCCTGCACAAGGCCTTTGTGGAGGTTACAGAGGAGGGAGCAGAA
GCTGCAGCTGCCACCGCTGTAGTAGGATTCGGATCATCACCTACTTCAACTAAT
GAAGAGTTCCATTGTAATCACCCTTTCCTATTCTTCATAAGGCAAAATAAGACC
AACAGCATCCTCTTCTATGGCAGATTCTCATCCCCGTAG
```

FIG. 3

Amino Acid Sequence of Psoriastatin 1,

```
            1                                                          50
Psolprotein MNSLSEANTK FMFDLFQQFR KSKEN.NIFY SPISITSALG MVLLGAKDNT
            51                                                         100
Psolprotein AQQIKKVLHF DQVTENTTGK AATYHVDRSG DVHHQFQKLL TEFNKSTDAY
            101                                                        150
Psolprotein ELKIANKLFG EKTYLFLQEY LDAIKKFYQT SVESVDFANA PEESRKKINS
            151                                                        200
Psolprotein WVESQTNEKI KNLIPEGNIG SNTTLVLVNA IYFKGQWEKK FNKEDTKEEK
            201                                                        250
Psolprotein FWPNKNTYKS IQMMRQYTSF HFASLEDVQA KVLEIPYKGK DLSMIVLLPN
            251                                                        300
Psolprotein EIDGLQRLEE ELTAEKLMEW TSLQNMRETR VDLHLPRFKV EESYDLKDTL
            301                                                        350
Psolprotein RTMGMVDIFN .GDADLSGMT GSRGLVLSGV LHKAFVEVTE EGAEAAAATA
            351                              392
Psolprotein VVGFGSSPTS TNEEFHCNHP FLFFIRQNKT NSILFYGRFS SP
```

FIG. 4

Psoriastatin type-II DNA sequence

```
ATGAATTCACTCAGTGAAGCCAACACCAAGTTCATGTTCGATCTGTTCCAACAG
TTCAGAAAATCAAAAGAGAACAACATCTTCTATTCCCCTATCAGCATCACATCA
GCATTAGGGATGGTCCTCTTAGGAGCCAAAGACAACACTGCACAACAAATTAGC
AAGGTTCTTCACTTTGATCAAGTCACAGAGAACACCACAGAAAAAGCTGCAACA
TATCATGTTGATAGGTCAGGAAATGTTCATCACCAGTTTCAAAAGCTTCTGACT
GAATTCAACAAATCCACTGATGCATATGAGCTGAAGATCGCCAACAAGCTCTTC
GGAGAAAAGACGTATCAATTTTTACAGGAATATTTAGATGCCATCAAGAAATTT
TACCAGACCAGTGTGGAATCTACTGATTTTGCAAATGCTCCAGAAGAAAGTCGA
AAGAAGATTAACTCCTGGGTGGAAAGTCAAACGAATGAAAAAATTAAAAACCTA
TTTCCTGATGGGACTATTGGCAATGATACGACACTGGTTCTTGTGAACGCAATC
TATTTCAAAGGGCAGTGGGAGAATAAATTTAAAAAAGAAAACACTAAAGAGGAA
AAATTTTGGCCAAACAAGAATACATACAAATCTGTACAGATGATAAGGCAATAC
AATTCCTTTAATTTTGCCTTGCTTGAGGATGTACAGGCCAAGGTCCTGGAAATA
CCATACAAAGGCAAGATCTAAGCATGATTGTGCTGCTGCCAAATGAAATCGAT
GGTCTGCAGAAGCTTGAAGAGAAACTCACTGCTGAGAAATTGATGGAATGGACA
AGTTTGCAGAATATGAGAGAGACATGTGTCGATTTACACTTACCTCGGTTCAAA
ATGGAAGAGAGCTATGACCTCAAGGACACGTTGAGAACCATGGGAATGGTGAAT
ATCTTCAATGGGGATGCAGACCTCTCAGGCATGACCTGGAGCCACGGTCTCTCA
GTATCTAAAGTCCTACACAAGGCCTTTGTGGAGGTCACTGAGGAGGGAGTGGAA
GCTGCAGCTGCCACCGCTGTAGTAGTAGTCGAATTATCATCTCCTTCAACTAAT
GAAGAGTTCTGTTGTAATCACCCTTTCCTATTCTTCATAAGGCAAAATAAGACC
AACAGCATCCTCTTCTATGGCAGATTCTCATCCCCGTAG
```

FIG. 5

Amino Acid Sequence of Psoriastatin 2

```
             1
Pso2protein  MNSLSEANTK FMFDLFQQFR KSKEN.NIFY SPISITSALG MVLLGAKDNT    50

51
Pso2protein  AQQISKVLHF DQVTENTTEK AATYHVDRSG NVHHQFQKLL TEFNKSTDAY    100

101
Pso2protein  ELKIANKLFG EKTYQFLQEY LDAIKKFYQT SVESTDFANA PEESRKKINS    150

151
Pso2protein  WVESQTNEKI KNLFPDGTIG NDTTLVLVNA IYFKGQWENK FKKENTKEEK    200

201
Pso2protein  FWPNKNTYKS VQMIRQYNSF NFALLEDVQA KVLEIPYKGK DLSMIVLLPN    250

251
Pso2protein  EIDGLQKLEE KLTAEKLMEW TSLQNMRETC VDLHLPRFKM EESYDLKDTL    300

301
Pso2protein  RTMGMVNIFN .GDADLSGMT WSHGLSVSKV LHKAFVEVTE EGVEAAAATA    350

351
Pso2protein  VVVVELSSPS TNEEFCCNHP FLFFIRQNKT NSILFYGRFS SP            392
```

FIG. 6

TWO NOVEL GENES FROM PSORIATIC EPIDERMIS: PSORIASTATIN TYPE I AND PSORIASTATIN TYPE II

This application claims benefit from the Previously filed Provisional Application No. 60/013,755 filed Mar. 20, 1996 and from 60/005,679 filed on Oct. 17, 1995, which are hereby incorporated by reference.

FIELD OF THE INVENTION

The invention relates to the psoriastatin type I and II genes, psoriastatin type I; and II polypeptides, and methods of using psoriastatin nucleic acids and polypeptides.

BACKGROUND OF THE INVENTION

Psoriasis is a disease chacterized by abnormal proliferation of keratinocytes and inflammation of the involved skin. A variety of proteinases which are not found in normal epidermis has been reported to appear in such skin.

SUMMARY OF THE INVENTION

In general, the invention features a psoriastatin type I polypeptide, e.g., a polypeptide, the sequence of which includes, or is, all or part of the sequence shown in SEQ ID NO:2. Preferred embodiments include fragments and analogs of SEQ ID NO:2, preferably having at least one biological activity of a psoriastatin type I polypeptide.

In preferred embodiments, the polypeptide is a recombinant or a substantially pure preparation of a psoriastatin type I polypeptide.

In preferred embodiments, the residue at position 357 (according to the numbering system used herein) is: other than alanine; a residue having a side chain group of greater molecular weight from the side chain group of alanine; a basic residue; an acidic residue; a threonine.

In preferred embodiments: the polypeptide has at least one biological activity, e.g., it reacts with an antibody, or antibody fragment, specific for a psoriastatin type I polypeptide; the polypeptide includes an amino acid sequence at least 60%, 80%, 90%, 95%, 98%, or 99% homologous to an amino acid sequence from SEQ ID NO:2; the polypeptide includes an amino acid sequence essentially the same as an amino acid sequence in SEQ ID NO:2; the polypeptide is at least 5, 10, 20, 50, 100, 150, 200, or 250 amino acids in length; the polypeptide includes at least 5, preferably at least 10, more preferably at least 20, most preferably at least 50, 100, 150, 200, or 250 contiguous amino acids from SEQ ID NO:2; the polypeptide is preferably at least 10, but no more than 100, amino acids in length; the psoriastatin type I polypeptide is either, an agonist or an antagonist, of a biological activity of a naturally occurring psoriastatin type I polypeptide.

In preferred embodiments: the psoriastatin type I polypeptide is encoded by the nucleic acid sequence of SEQ ID NO:1, or by a nucleic acid having at least 60%, 70%, 80%, 90%, 95%, 98%, or 99% homology with the nucleic acid of SEQ ID NO:1. For example, the psoriastatin type I polypeptide can be encoded by a nucleic acid sequence which differs from a nucleic acid sequence of SEQ ID NO:1 due to degeneracy in the genetic code.

In a preferred embodiment the psoriastatin type I polypeptide is an agonist of a naturally-occurring mutant or wild type psoriastatin type I polypeptide (e.g., a polypeptide having an amino acid sequence shown in SEQ ID NO:2). In another preferred embodiment, the polypeptide is an antagonist which, for example, inhibits an undesired activity of a naturally-occurring psoriastatin type I polypeptide (e.g., a mutant polypeptide).

In a preferred embodiment, the psoriastatin type I polypeptide differs in amino-acid sequence at 1, 2, 3, 5, 10 or more residues, from a sequence in SEQ ID NO:2. The differences, however, are such that the psoriastatin type I polypeptide exhibits at least one biological activity of a psoriastatin type I polypeptide, e.g., the psoriastatin type I polypeptide retains a biological activity of a naturally occurring psoriastatin type I polypeptide.

In preferred embodiment the psoriastatin type I polypeptide includes a psoriastatin type I polypeptide sequence, as described herein, as well as other N-terminal and/or C-terminal amino acid sequences.

In preferred embodiments, the polypeptide includes all or a fragment of an amino acid sequence from SEQ ID NO:2, fused, in reading frame, to additional amino acid residues, preferably to residues encoded by genomic DNA 5' to the genomic DNA which encodes a sequence from SEQ ID NO:2.

In yet other preferred embodiments, the psoriastatin type I polypeptide is a recombinant fusion protein having a first psoriastatin type I polypeptide portion and a second polypeptide portion having an amino acid sequence unrelated to a psoriastatin type I polypeptide. The second polypeptide portion can be, e.g., any of glutathione-S-transferase, a DNA binding domain, or a polymerase activating domain. In preferred embodiment the fusion protein can be used in a two-hybrid assay.

In a preferred embodiment, the psoriastatin type I polypeptide is a fragment or analog of a naturally occurring psoriastatin type I polypeptide which inhibits reactivity with antibodies, or F(ab')$_2$ fragments, specific for a naturally occurring psoriastatin type I polypeptide.

In a preferred embodiment, the psoriastatin type I polypeptide includes a sequence which is not present in the mature protein.

In a preferred embodiment, the psoriastatin type I polypeptide has a molecular weight of about 43 kDa.

In preferred embodiments, the psoriastatin type I polypeptide has one or more of the following properties: the residue at position 357 is other than alanine: has a molecular weight of about 43 kDa; can be isolated from psoriatic tissue; is expressed in psoriatic tissue. e.g., psoriatic epidermis, at least 2, and preferably at least 5 or 10 times more abundantly than in normal tissue; is a cross-class inhibitor (e.g., it inhibits cysteine proteinases, e.g., cathepsin L. but does not inhibit serine proteinases); inhibits cathepsin L at least 2. more preferably at least 2, 5, 10, or 100 times less efficiently than does squamous cell carcinoma-antigen (SCC-A); inhibits cathepsin L but not cathepsin B or cathepsin H; is active at pH 5.0; is secreted.

Polypeptides of the invention include those which arise as a result of the existence of multiple genes, alternative transcription events, alternative RNA splicing events, and alternative translational and postranslational events.

The invention includes an immunogen which includes an active or inactive psoriastatin type I polypeptide, or an analog or a fragment thereof, in an immunogenic preparation, the immunogen being capable of eliciting an immune response specific for the psoriastatin type I polypeptide, e.g., a humoral response, an antibody response, or a cellular response. In preferred embodiments, the immunogen comprising an antigenic determinant, e.g., a unique determinant, from a protein represented by SEQ ID NO:2.

The invention also includes an antibody preparation, preferably a monoclonal antibody preparation, specifically reactive with an epitope of the psoriastatin type I immunogen or generally of a psoriastatin type I polypeptide.

In another aspect, the invention provides a substantially pure nucleic acid having, or comprising, a nucleotide sequence which encodes a polypeptide, the amino acid sequence of which includes, or is, the sequence of a psoriastatin type I polypeptide, or analog or fragment thereof.

In preferred embodiments, the nucleic acid encodes a polypeptide having one or more of the following characteristics: at least one biological activity of a psoriastatn type I polypeptide, e.g., a polypeptide specifically reactive with an antibody, or antibody fragment, directed against a psoriastatin type I polypeptide; an amino acid sequence at least 60%, 80%, 90%, 95%, 98%, or 99% homologous to an amino acid sequence from SEQ ID NO:2; an amino acid sequence essentially the same as an amino acid sequence in SEQ ID NO:2, the polypeptide is at least 5, 10, 20, 50, 100, 150, 200, or 250 amino acids in length; at least 5, preferably at least 10, more preferably at least 20, most preferably at least 50, 100, 150, 200, or 250 contiguous amino acids from SEQ ID NO:2; an amino acid sequence which is preferably at least 10, but no more than 100, amino acids in length; the ability to act as an agonist or an antagonist of a biological activity of a naturally occurring psoriastatin type I polypeptide.

In preferred embodiments: the nucleic acid is or includes the nucleotide sequence of SEQ ID NO:1; the nucleic acid is at least 60%, 70%, 80%, 90%, 95%, 98%, or 99% homologous with a nucleic acid sequence of SEQ ID NO:1; the nucleic acid includes a fragment of SEQ ID NO:1 which is at least 25, 50, 100, 200, 300, 400, 500, or 1,000 bases in length; the nucleic acid differs from the nucleotide sequence of SEQ ID NO:1 due to degeneracy in the genetic code.

In preferred embodiments: the nucleotide residue at position 161 is other than an adenine nucleotide, e.g., it is a guanine nucleotide; the nucleotide residue at position 259 is other than an adenine nucleotide, e.g. it is a guanine nucleotide; the nucleotide residue at position 788 is other than an adenine nucleotide, e.g., it is a guanine nucleotide; the nucleotide residue at position 799 is other than an adenine nucleotide, e.g., it is a guanine nucleotide; the nucleotide residue at position 1008 is other than an adenine nucleotide, e.g., it is a guanine nucleotide; the nucleotide residue at position 1090 is other than a guanine nucleotide, e.g., it is an adenine nucleotide.

In a preferred embodiment the polypeptide encoded by the nucleic acid is an agonist which, for example, is capable of enhancing an activity of a naturally-occurring mutant or wild type psoriastatin type I polypeptide. In another preferred embodiment, the encoded polypeptide is an antagonist which, for example, inhibits an undesired activity of a naturally-occurring psoriastatin type I polypeptide (e.g., a polypeptide having an amino acid sequence shown in SEQ ID NO:2).

In a preferred embodiment, the encoded psoriaststin type I polypeptide differs in amino acid sequence at 1, 2, 3, 5, 10 or more residues, from a sequence in SEQ ID NO:2. The differences, however, are such that the encoded psoriastatin type I polypeptide exhibits at least one biological activity of a naturally occurring psoriastatin type I polypeptide (e.g., the psoriastatin type I polypeptide of SEQ ID NO:2).

In preferred embodiments, the nucleic acid encodes a psoriastatin type I polypeptide which includes a psoriastatin type I polypeptide sequence, as described herein, as well as other N-terminal and/or C-terminal amino acid sequences.

In preferred embodiments, the nucleic acid encodes a polypeptide which includes all or a portion of an amino acid sequence shown in SEQ ID NO:2, fused, in reading frame, to additional amino acid residues, preferably to residues encoded by genomic DNA 5' to the genomic DNA which encodes a sequence from SEQ ID NO:2.

In preferred embodiments, the encoded polypeptide is a recombinant fusion protein having a first psoriastatin type I polypeptide portion and a second polypeptide portion having an amino acid sequence unrelated to a psoriastatin type I polypeptide. The second polypeptide portion can be, e.g., any of glutathione-S-transferase; a DNA binding domain; or a polymerase activating domain. In preferred embodiments the fusion protein can be used in a two-hybrid assay.

In preferred embodiments, the encoded polypeptide is a fragment or analog of a naturally occurring psoriastatin type I polypeptide which inhibits reactivity with antibodies, or F(ab')$_2$ fragments, specific for a naturally occurring psoriastatin type I polypeptide.

In preferred embodiments, the nucleic acid will include a transcriptional regulatory sequence, e.g. at least one of a transcriptional promoter or transcriptional enhancer sequence, operably linked to the psoriastatin type I gene sequence.e.g., to render the psoriastatin type I gene sequence suitable for use as an expression vector.

In yet another preferred embodiment, the nucleic acid of the invention hybridizes under stringent conditions to a nucleic acid probe corresponding to at least 12 consecutive nucleotiles from SEQ ID NO:1. or more preferably to at least 20 consecutive nucleotides from SEQ ID NO:1, or more preferably to at least 40 consecutive nucleotides from SEQ ID NO:1.

In a preferred embodiment, the nucleic acid encodes a mature polypeptide having a molecular weight of about 43 kDa.

In a preferred embodiment, the nucleic acid encodes a psoriastatin type I polypeptide which includes a sequence which is not present in the mature protein.

In preferred embodiments, the nucleic acid encodes a psoriastatin type I polypeptide which has one or more of the following properties: the residue at position 357 is other than alanine; has a molecular weight of about 43 kDa; can be isolated from psoriatic tissue; is expressed in psoriatic tissue, e.g., psoriatic epidermis, at least 2, and preferably at least 5 or 10 times more abundantly than in normal tissue; is a cross-class inhibitor (e.g., it functionally inhibits cysteine proteinases, e.g., cathepsin L, but does not inhibit serine proteinases); inhibits cathepsin L at least 2, more preferably at least 2, 5, 10, or 100 times less. efficiently than does squamous cell carcinoma-antigen (SCC-A); inhibits cathepsin L but not cathepsin B or cathepsin H; is active at pH 5.0; is secreted.

In another aspect, the invention includes: a vector including a nucleic acid which encodes a psoriastatin type I polypeptide, e.g., a psoriastatin type I polypeptide; a host cell transfected with the vector; and a method of producing a recombinant psoriastatin type I like polypeptide, e.g., a psoriastatin type I polypeptide; including culturing the cell, e.g., in a cell culture medium, and isolating the psoriastatin type I-like polypeptide, e.g., a psoriastatin type I polypeptide, e.g., from the cell or from the cell culture medium.

In another aspect, the invention features, a purified recombinant nucleic acid having at least 50%, 60%, 70%, 80%, 90%, 95%, 98%, or 99% homology with a nucleotide sequence shown in SEQ ID NO:1.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:1, or naturally occurring mutants thereof. In preferred embodiments, the probe or primer further includes a label group attached thereto. The label group can be, e.g., a radioisotope, a fluorescent compound, an enzyme, and/or an enzyme co-factor. Preferably the oligonucleotide is at least 10 and less than 20, 30, 50, 100, or 150 nucleotides in length.

The invention involves nucleic acids, e.g., RNA or DNA, encoding a polypeptide of the invention. This includes double stranded nucleic acids as well as coding and antisense single strands.

In general, the invention features a psoriastatin type II polypeptide, e.g., a polypeptide, the sequence of which includes, or is, all or part of the sequence shown in SEQ ID NO:4. Preferred embodiments include fragments and analogs of SEQ ID NO:4, preferably having at least one biological activity of a psoriastatin type II polypeptide.

In preferred embodiments, the polypeptide is a recombinant or a substantially pure preparation of a psoriastatin type II polypeptide.

In preferred embodiments: the reactive site of the psoriastatin type II polypeptide, e.g., amino acid residues 351–357 (according to the numbering system used herein) have no homology or are less than about 25%, more preferably less than about 42%, 57%, 71% or 85% homologous with the corresponding residues of SCC-A; residues 351–357 are other than GFGSSPA (SEQ ID NO:5); residues 351–357 are WELSSP (SEQ ID NO:6), or a sequence with at least about 14%, 28%, 42%, 057%, 071% or 85% homology therewith In preferred embodiments: the polypeptide has at least one biological activity, e.g., it reacts with an antibody, or antibody fragment, specific for a psoriastatin type II polypeptide; the polypeptide includes an amino acid sequence at least 60%, 80%, 90%, 95%, 98%, or 99% homologous to an amino acid sequence from SEQ ID NO:4; the polypeptide includes an amino acid sequence essentially the same as an amino acid sequence in SEQ ID NO:4; the polypeptide is at least 5, 10, 20, 50, 100, 150, 200, or 250 amino acids in length; the polypeptide includes at least 5, preferably at least 10, more preferably at least 20, most preferably at least 50, 100, 150, 200, or 250 contiguous amino acids from SEQ ID NO:4; the polypeptide is preferably at least 10, but no more than 100, amino acids in length; the psoriastatin type II polypeptide is either, an agonist or an antagonist, of a biological activity of a naturally occurring psoriastatin type II polypeptide.

In preferred embodiments: the psoriastatin type II polypeptide is encoded by the nucleic acid sequence of SEQ ID NO:3, or by a nucleic acid having at least 60%, 70%, 80%, 90%, 95%, 98%, or 99% homology with the nucleic acid of SEQ ID NO:3. For example, the psoriastatin type II polypeptide can be encoded by a nucleic acid sequence which differs from a nucleic acid sequence of SEQ ID NO:3 due to degeneracy in the genetic code.

In a preferred embodiment the psoriastatin type II polypeptide is an agonist of a naturally-occurring mutant or wild type psoriastatin type II polypeptide (e.g., a polypeptide having an amino acid sequence shown in SEQ ID NO:4). In another preferred embodiment, the polypeptide is an antagonist which, for example, inhibits an undesired activity of a naturally-occurring psoriastatin type II polypeptide (e.g., a mutant polypeptide).

In a preferred embodiment, the psoriastatin type II polypeptide differs in amino acid sequence at 1, 2, 3, 5, 10 or more residues, from a sequence in SEQ ID NO:4. The differences, however, are such that the psoriastatin type II polypeptide exhibits at least one biological activity of a psoriastatin type II polypeptide, e.g., the psoriastatin type II polypeptide retains a biological activity of a naturally occurring psoriastatin type II polypeptide.

In preferred embodiments the psoriastatin type II polypeptide includes a psoriastatin type II polypeptide sequence, as described herein, as well as other N-terminal and/or C-terminal amino acid sequences.

In preferred embodiments, the polypeptide includes all or a fragment of an amino acid sequence from SEQ ID NO:4, fused, in reading frame, to additional amino acid residues, preferably to residues encoded by genomic DNA 5' to the genomic DNA which encodes a sequence from SEQ ID NO:4.

In yet other preferred embodiments, the psoriastatin type II polypeptide is a recombinant fusion protein having a first psoriastatin type I polypeptide portion and a second polypeptide portion having an amino acid sequence unrelated to a psoriastatin type II polypeptide. The second polypeptide portion can be, e.g., any of glutathione-S-transferase, a DNA binding domain, or a polymerase activating domain In preferred embodiment the fission protein can be used in a two-hybrid assay.

In a preferred embodiment, the psoriastatin type II polypeptide is a fragment or analog of a naturally occurring psoriastatin type II polypeptide which inhibits reactivity with antibodies, or F(ab')$_2$ fragments, specific for a naturally occurring psoriastatin type II polypeptide.

In a preferred embodiment, the psoriastatin type II polypeptide includes a sequence which is not present in the mature protein.

In a preferred embodiment, the psoriastatin type II polypeptide has a molecular weight of about 43 kDa:

Polypeptides of the invention include those which arise as a result of the existence of multiple genes, alternative transcription events, alternative RNA splicing events, and alternative translational and postranslational events.

In preferred embodiments, the psoriastatin type II polypeptide: has a molecular weight of about 43 kDa; can be isolated from psoriatic tissue; is expressed in psoriatic tissue, e.g., psoriatic epidernis, at least 2, and preferably at least 5 or 10 times more abundantly than in normal tissue; is localized in the nucleus of the cell in psoriatic tissue.

The invention includes an immunogen which includes an active or inactive psoriastatin type II polypeptide, or an analog or a fragment thereof, in an immunogenic preparation, the immunogen being capable of eliciting an immune response specific for the psoriastatin type II polypeptide, e.g., a humoral response, an antibody response, or a cellular response. In preferred embodiments, the immunogen comprising an antigenic determinant, e.g., a unique determinant, from a protein represented by SEQ ID NO:4.

The invention also includes an antibody preparation, preferably a monoclonal antibody preparation, specifically reactive with an epitope of the psoriastatin type II immunogen or generally of a psoriastatin type II polypeptide.

In another aspect, the invention provides a substantially pure nucleic acid having, or comprising, a nucleotide sequence which encodes a polypeptide, the amino acid sequence of which includes, or is, the sequence of a psoriastatin type II polypeptide, or analog or fragment thereof.

In preferred embodiments: the nucleic acid encodes a reactive site of the psoriastatin type II polypeptide, e.g., amino acid residues 351–357 (according to the numbering system used herein) have no homology or are less than about 25%, more preferably less than about 42%, 57%, 71% or 85% homologous with the corresponding residues of SCC-A; residues 351–357 are other than GFGSSPA (SEQ ID NO:5); residues 351–357 are VVELSSP (SEQ ID NO:6), or a sequence with at least about 14%, 28%, 42%, 57%, 71% or 85% homology therewith.

In preferred embodiments, the nucleic acid encodes a polypeptide having one or more of the following characteristics: at least one biological activity of a psoriastatin type II polypeptide, e.g., a polypeptide specifically reactive with an antibody, or antibody fragment, directed against a psoriastatin type II polypeptide; an amino acid sequence at least; 60%, 80%, 90%, 95%, 98%, or 99% homologous to an amino acid sequence from SEQ ID NO:4; an amino acid sequence essentially the same as an amino acid sequence in SEQ ID NO:4, the polypeptide is at least 5, 10, 20, 50, 100, 150, 200, or 250 amino acids in length; at: least 5, preferably at least 10, more preferably at least 20, most preferably at least 50, 100, 150, 200, or 250 contiguous amino acids from SEQ ID NO:4; an amino acid sequence which is preferably at least 10, but no more than 100, amino acids in length; the ability to act as an agonist or an antagonist of a biological activity of a naturally occurring psoriastatin type II polypeptide.

In preferred embodiments: the nucleic acid is or includes the nucleotide sequence of SEQ ID NO:3; the nucleic acid is at least 60%, 70%, 80%, 90%, 95%, 98%, or 99% homologous with a nucleic acid sequence of SEQ ID NO:3; the nucleic acid includes a fragment of SEQ ID NO:3 which is at least 25, 50, 100, 200, 300, 400, 500, or 1,000 bases in length; the nucleic acid differs from the nucleotide sequence of SEQ ID NO:3 due to degeneracy in the genetic code.

In a preferred embodiment the polypeptide encoded by the nucleic acid is an agonist which, for example, is capable of enhancing an activity of a naturally-occurring mutant or wild type psoriastatin type II polypeptide. In another preferred embodiment, the encoded polypeptide is an antagonist which, for example, inhibits an undesired activity of a naturally-occurring psoriastatin type II polypeptide (e.g., a polypeptide having an amino acid sequence shown in SEQ ID NO:4).

In a preferred embodiment, the encoded psoriastatin type II polypeptide differs in amino acid sequence at 1, 2, 3, 5, 10 or more residues, from a sequence in SEQ ID NO:4. The differences, however, are such that the encoded psoriastatin type II polypeptide exhibits at least one biological activity of a naturally occurring psoriastatin type II polypeptide (e.g., the psoriastatin type II polypeptide of SEQ ID NO:4).

In preferred embodiments, the nucleic acid encodes a psoriastatin type II polypeptide which includes a psoriastatin type II polypeptide sequence, as described herein, as well as other N-terminal and/or C-terminal amino acid sequences.

In preferred embodiments, the nucleic acid encodes a polypeptide which includes all or a portion of an amino acid sequence shown in SEQ ID NO:4, fused, in reading frame, to additional amino acid residues, preferably to residues encoded by genomic DNA 5' to the genomic DNA which encodes a sequence from SEQ ID NO:4.

In preferred embodiments, the encoded polypeptide is a recombinant fusion protein having a first psoriastatin type II polypeptide portion and a second polypeptide portion having an amino acid sequence unrelated to a psoriastatin type II polypeptide. The second polypeptide portion can be, e.g., any of glutathione-S-transferase; a DNA binding domain; or a polymerase activating domain. In preferred embodiments the fusion protein cane be used in a two-hybrid assay.

In preferred embodiments, the encoded polypeptide is a fragment or analog of a naturally occurring psoriastatin type II polypeptide which inhibits reactivity with antibodies, or F(ab')$_2$ fragments, specific for a naturally occurring psoriastatin type II polypeptide.

In preferred embodiments, the nucleic acid will include a transcriptional regulatory sequence, e.g. at least one of a transcriptional promoter or transcriptional enhancer sequence, operably linked to the psoriastatin type II gene sequence, e.g., to render the psoriastatin type II gene sequence suitable for use as an expression vector.

In yet another preferred embodiment, the nucleic acid of the invention hybridizes under stringent conditions to a nucleic acid probe corresponding to at least 12 consecutive nucleotides from SEQ ID NO:3, or more preferably to at least 20 consecutive nucleotides from SEQ ID NO:3, or more preferably to at least 40 consecutive nucleotides from SEQ ID NO:3.

In a preferred embodiment, the nucleic acid encodes a mature polypeptide having a molecular weight of about 43 kDa.

In a preferred embodiment, the nucleic acid encodes a psoriastatin type II polypeptide which includes a sequence which is not present in the mature protein.

In preferred embodiments, the nucleic acid encodes a psoriastatin type II polypeptide which: has a molecular weight of about 43 kDa; can be isolated from psoriatic tissue; is expressed in psoriatic tissue, e.g., psoriatic epidermis, at least 2, and preferably at least 5 or 10 times more abundantly than in normal tissue; is localized in the nucleus of the cell in psoriatic tissue.

In another aspect, the invention includes: a vector including a nucleic acid which encodes a psoriastatin type II polypeptide, e.g., a psoriastatin type II polypeptide; a host cell transfected with the vector; and a method of producing a recombinant psoriastatin type II-like polypeptide, e.g., a psoriastatin type II polypeptide; including culturing the cell, e.g., in a cell culture medium, and isolating the psoriastatin type II-like polypeptide, e.g., a psoriastatin type II polypeptide, e.g., from the cell or from the cell culture medium.

In another aspect, the invention features, a purified recombinant nucleic acid having at least 50%, 60%, 70%, 80%, 90%, 95%, 98%, or 99% homology with a nucleotide sequence shown in SEQ ID NO:3.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:3, or naturally occurring mutants thereof. In preferred embodiments, the probe or primer further includes a label group attached thereto. The label group can be, e.g., a radioisotope, a fluorescent compound, an enzyme, and/or an enzyme co-factor. Preferably the oligonucleotide is at least 10 and less than 20, 30, 50, 100, or 150 nucleotides in length.

The invention involves nucleic acids, e.g., RNA or DNA, encoding a polypeptide of the invention. This includes double stranded nucleic acids as well as coding and antisense single strands.

In another aspect, the invention features a method of evaluating a compound for the ability to interact with, e.g., bind, or modulate, e.g., inhibit or promote, the activity of a psoriastatin polypeptide, e.g., a psoriastatin type I or a psoriastatin type II polypeptide. The method includes contacting the compound with the psoriastatin polypeptide, and evaluating ability of the compound to interact with or form a complex with the psoriastatin polypeptide. This method can be performed in vitro, e.g., in a cell free system, or in vivo, e.g., in a two-hybrid interaction trap assay. This method can be used to identify naturally occurring molecules which interact with psoriastatin polypeptides, e.g., psoriastatin type I or psoriastatin type II polypeptides. It can also be used to find natural or synthetic inhibitors of mutant or wild type psoriastatin polypeptides, e.g., psoriastatin type I or psoriastatin type II polypeptides. The compound can be a peptide or a non peptide molecule, e.g., a small molecule preferably 500 to 5,000 molecular weight, more preferably 500 to 1,000 molecular weight, having an aromatic scaffold, e.g., bis-amide phenols, decorated with various functional groups.

In brief, a two hybrid assay system (see e.g., Bartel et al. (1993) *Cellular Interaction in Development: A practical Approach*, D. A. Hartley, ed., Oxford University Press, Oxford, pp. 153–179) allows for detection of protein—protein interactions in yeast cells. The known protein, e.g., a psoriastatin polypeptide, is often referred to as the "bait" protein. The proteins tested for binding to the bait protein are often referred to as "fish" proteins. The "bait" protein, e.g., a psoriastatin polypeptide, is fused to the GAL4 DNA binding domain. Potential "fish" proteins are fused to the GAL4 activating domain. If the "bait" protein and a "fish" protein interact, the two GAL4 domains are brought into close proximity, thus rendering the host yeast cell capable of surviving a specific growth selection.

In another aspect, the invention features a method of identifying active fragments or analogs of a psoriastatin polypeptide, e.g., a psoriastatin type I or a psoriastatin type II polypeptide. The method includes first identifying a compound, e.g., cathepsin L, which interacts with a psoriastatin polypeptide and determining the ability of the compound to bind the fragment or analog. The two hybrid assay described above can be used to obtain fragment-binding compounds. These compounds can then be used as "bait" to fish for and identify fragments of the psoriastatin polypeptide which interact, bind, or form a complex with these compounds.

In another aspect, the invention features a method of making a psoriastatin polypeptide, e.g., a psoriastatin type I or a psoriastatin type II polypeptide, having a non-wild amino acid sequence, e.g., an antagonist, agonist, or super agonist of a naturally occurring psoriastatin polypeptide, e.g., the psoriastatin type I or psoriastatin type II polypeptide. The method includes altering the sequence of a psoriastatin polypeptide (e.g., SEQ ID NO:2 or SEQ ID NO:4) by, for example, substitution or deletion of one or more residues of a conserved or non-conserved region, and testing the altered polypeptide for the desired activity, e.g., the ability to modulate, e.g., inhibit or promote, apoptosis or cell growth.

In another aspect, the invention features a method of making a psoriastatin polypeptide, e.g., a psoriastatin type I or a psoriastatin type II polypeptide, having a non-wild type activity, e.g., an antagonist, agonist, or super agonist of a naturally occurring psoriastatin polypeptide, e.g., the psoriastatin type I or psoriastatin type II polypeptide. The method includes altering the sequence of a psoriastatin polypeptide (e.g., SEQ ID NO:2 or SEQ ID NO:4) by, for example, substitution or deletion of one or more residues of a conserved or non-conserved region, and testing the altered polypeptide for the desired activity, e.g., the ability to modulate, e.g., inhibit or promote, apoptosis or cell growth.

In another aspect, the invention features a method of making a fragment or analog of a psoriastatin polypeptide e.g., a psoriastatin type I or a psoriastatin type II polypeptide, e.g., a psoriastatin polypeptide having at least one biological activity of a naturally occurring psoriastatin polypeptide. The method includes altering the sequence, e.g., by substitution or deletion of one or more residues, preferably which are conserved or non-conserved residues, of a psoriastatin polypeptide, and testing the altered polypeptide for the desired activity, e.g., the ability to modulate, e.g., inhibit or promote, apoptosis or cell growth.

In another aspect, the invention features a method of evaluating a compound for the ability to modulate psoriastatin polypeptide-, e.g., a psoriastatin type I or II polypeptide-, mediated regulation of cathepsin L. The method includes: contacting the compound with either or both of a psoriastatin polypeptide and cathepsin L, and determining the effect of the compound on the ability of psoriastatin to inhibit cathepsin L.

In another aspect, the invention features a method of evaluating a compound for the ability to modulate cathepsin L activity. The method includes: contacting the compound with either or both of psoriastatin polypeptide (e.g., psoriastatin type I or II polypeptide) and cathepsin L, and determining the effect of the compound on the activity of cathepsin L.

In another aspect, the invention features a method of treating a mammal, e.g., a human. The method includes administering to the mammal a therapeutically effective amount a substance which modulates an activity of psoriastatin type I or psoriastatin type II.

In another aspect, the invention features a method of treating a mammal e.g., a human, at risk for a disorder characterized by unwanted cell proliferation or less than wild type levels of apoptosis, e.g., cancer or psoriasis. The method includes administering to the mammal a treatment which modulates, e.g., inhibits, an activity of psoriastatin type I or psoriastatin type II, e.g., administering a therapeutically effective amount of a nucleic acid encoding an antagonist of a psoriastatin polypeptide, e.g., a psoriastatin type I or a psoriastatin type II polypeptide.

In another aspect, the invention features a method of treating a mammal, e.g., a human, at risk for a disorder characterized by unwanted cell proliferation or less than wild type levels of apoptosis, e.g., cancer or psoriasis. The method includes administering to the mammal a treatment which modulates, e.g., inhibits, an activity of psoriastatin type I or psoriastatin type II, e.g., administering a therapeutically effective amount of an antagonist of a psoriastatin polypeptide, e.g., an antagonist of a psoriastatin type I or a psoriastatin type II in polypeptide.

In preferred embodiments, the antagonist of psoriastatin polypeptide is: an antisense psoriastatin nucleic acid or an anti-psoriastatin antibody.

In another aspect, the invention features, a method of evaluating a compound for the ability to bind a nucleic acid encoding a psoriastatin, e.g., a psoriastatin type I or type II, gene regulatory sequence. The method includes: contacting the compound with the nucleic acid; and evaluating ability of the compound to form a complex with the nucleic acid. In preferred embodiments the psoriastatin gene regulatory sequence is functionally linked to a heterologous gene, e.g., a reporter gene.

In another aspect, the invention features a human cell, e.g., a fibroblast or a dermal cell, e.g., a keratinocyte, transformed with a nucleic acid which encodes a psoriastatin polypeptide, e.g., a psoriastatin type I or a psoriastatin type II polypeptide.

In another aspect, the invention includes: an expression vector containing a nucleic acid encoding a psoriastatin polypeptide (e.g., SEQ ID NO:2 or SEQ ID NO:4), or an analog or fragment thereof; a cell transformed with an expression vector containing a nucleic acid encoding a psoriastatin polypeptide (e.g., SEQ ID NO:2 or SEQ ID NO:4), or an analog or fragment thereof; and a psoriastatin polypeptide made by culturing a cell transformed with an expression vector containing a nucleic acid encoding a psoriastatin polypeptide (e.g., SEQ ID NO:2 or SEQ ID NO:4), or an analog or fragment thereof.

In another aspect, the invention includes a transgenic animal, preferably a mammal, e.g., a mouse, rat, pig or goat, having a psoriastatin type I or psoriastatin type II transgene, e.g., a psoriastatin type I or psoriastatin type II gene having a deletion of all or a part of the wild type psoriastatin type I or psoriastatin type II gene. The transgenic animal can be heterozygous or homozygous for either or both of the transgenes.

Such a transgenic animal can serve as a model for studying disorders which are related to mutated or misexpressed psoriastatin type I or II gene alleles or for use in drug screening. For example, the invention includes a method of evaluating the effect of the expression or misexpression of a psoriastatin type I or II gene on a parameter related to modulation, e.g., stimulation or inhibition, of cell proliferation or apoptosis. The method includes: providing a transgenic animal having a psoriastatin, e.g., psoriastatin type I and/or II, transgene, or which otherwise misexpresses a psoriastatin, e.g., psoriastatin type I and/or II, gene; contacting the animal with an agent; and evaluating the effect of the transgene on the parameter related to modulation, e.g., stimulation or inhibition, of cell proliferation or apoptosis.

In another aspect, the invention features a method of modulating cell proliferation or apoptosis, e.g., inhibiting or promoting cell proliferation or apoptosis, which includes modulating psoriastatin activity, e.g., psoriastatin type I or psoriastatin type II activity, e.g., by administering a compound which inhibits or promotes psoriastatin activity.

In another aspect, the invention features a method of inhibiting cell proliferation or promoting apoptosis which includes inhibiting psoriastatin activity. e.g., psoriastatin type I or psoriastatin type II activity, e.g., by administering an effective amount of a compound which inhibits psoriastatin activity.

In preferred embodiments, the psoriastatin activity is inhibited by: contacting, a cell, e.g., a dermal cell, e.g., a keratinocyte, with an antagonist of a psoriastatin polypeptide, e.g., psoriastatin type I and/or psoriastatin type II polypeptide, an antisense psoriastatin, or an antipsoriastatin antibody.

In another aspect, the invention features a method of promoting cell proliferation or inhibiting apoptosis which includes promoting psoriastatin activity, e.g., psoriastatin type I or psoriastatin type II activity.

In preferred embodiments, the psoriastatin activity is promoted by: contacting a cell, e.g., a dermal cell, e.g., a keratinocyte, with a psoriastatin polypeptide, e.g., psoriastatin type I and/or psoriastatin type II polypeptide, or a psoriastatin polypeptide agonist In another aspect, the invention features a method of modulating, e.g., promoting or inhibiting, cathepsin L activity including contacting a cell with an effective amount of a psonastatin, e.g., a psoriastatin type I and/or II polypeptide.

In another aspect, the invention features a method of treating a skin disorder. e.g., psoriasis, including administering to a subject a therapeutically effective amount of a compound which inhibits psoriastatin, e.g., a psoriastatin type I and/or II. activity.

In preferred embodiments, the compound which inhibits psoriastatin activity is any of: a peptide antagonist, an antibody, or an antisense molecule.

In preferred embodiments, the subject is a mammal, e.g., a rodent, e.g., a mouse or a rat, or a primate, e.g., a human.

A "heterologous promoter", as used herein is a promoter which is not naturally associated with the psoriastatin, e.g., the psoriastatin type I or II, gene.

A "purified preparation" or a "substantially pure preparation" of a psoriastatin type I polypeptide, or a fragment or analog thereof, as used herein, means a psoriastatin type polypeptide, or a fragment or analog thereof, which is free of one or more other proteins including psoriastatin type II protein, lipids, and nucleic acids with which the psoriastatin type I polypeptide naturally occurs. Preferably, the polypeptide, or a fragment or analog thereof, is also separated from substances which are used to purify it, e.g., antibodies or gel matrix, such as polyacrylamide. Preferably, the polypeptide, or a fragment or analog thereof, constitutes at least 10, 20, 50 70, 80 or 95% dry weight of the purified preparation. Preferably, the preparation contains: sufficient polypeptide to allow protein sequencing; at least 1, 10, or 100 mg of the polypeptide; at least 1, 10, or 100 mg of the polypeptide.

A "purified preparation" or a "substantially pure preparation" of a psoriastatin type II polypeptide, or a fragment or analog thereof, as used herein, means a psoriastatin type II polypeptide, or a fragment or analog thereof, which is free from one or more other proteins including psoriastatin type I protein, lipids, and nucleic acids with which the psoriastatin type II polypeptide naturally occurs. Preferably, the polypeptide, or a fragment or analog thereof, is also separated from substances which are used to purify it. e.g., antibodies or gel matrix, such as polyacrylamide. Preferably, the polypeptide, or a fragment or analog thereof, constitutes at least 10, 20, 50 70, 80 or 95% dry weight of the purified preparation. Preferably, the preparation contains: sufficient polypeptide to allow protein sequencing; at least 1, 10, or 100 mg of the polypeptide; at least 1, 10, or 100 mg of the polypeptide.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

A "substantially pure nucleic acid". e.g., a substantially pure DNA encoding a psoriastatin type I or II polypeptide, is a nucleic acid which is one or both of: not immediately contiguous with one or both of the coding sequences with which it is immediately contiguous (i.e. one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional psoriastatin type I or II sequences.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The terms "peptides", "proteins", and "polypeptides" are used interchangeably herein.

As used herein, the term "tansgene" means a nucleic acid sequence (encoding e.g., one or more psoriastatin type I and/or II polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence, such as the psoriastatin, e.g., the psoriastatin type I or II, gene, operably linked to the promoter, and which effects expression of the selected DNA sequence in specific cells of a tissue, such as neurons. The term also covers so-called "leaky" promoters, which regulate expression of a selected DNA primarily in one tissue, but cause expression in other tissues as well.

A polypeptide has "at least one biological activity of a psoriastatin type I polypeptide" if it has one or more of the following properties: (1) the ability to react with an antibody, or antibody fragment, specific for (a) a wild type psoriastatin type I polypeptide, (b) a naturally-occurring mutant psoriastatin type I polypeptide, or (c) a fragment of either (a) or (b); (2) the ability to specifically inhibit cathepsin L activity; (3) the ability to promote cell proliferation or inhibit apoptosis; or (4) the ability to act as an antagonist or agonist of the activities recited in (1), (2) or (3).

A polypeptide has "at least one biological activity of a psoriastatin type II polypeptide" if it has one or more of the following properties: (1) the ability to react with an antibody, or antibody fragment, specific for (a) a wild type psoriastatin type II polypeptide, (b) a naturally-occurring mutant psoriastatin type II polypeptide, or (c) a fragment of either (a) or (b); (2) the ability to promote cell proliferation or inhibit apoptosis; (3) the ability to localize to the nucleus, or (4) the ability to act as an antagonist or agonist of the activities recited in (1), (2), or (3).

"Misexpression", as used herein, refers to a non-wild type pattern of psoriastatin type I or psoriastatin type II gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing, size, amino acid sequence, post-transitional modification, stability, or biological activity of the expressed psoriastatin type I or psoriastatin type II polypeptide; a pattern of expression that differs from wild type in terms of the effect of an environmental stimulus or extracellular stimulus on expression of the psoriastatin type I or psoriastatin type II gene, e.g., a pattern of increased or decreased expression (as compared with wild type) in the presence of an increase or decrease in the strength of the stimulus.

As described herein, one aspect of the invention features a pure (or recombinant) nucleic acid which includes a nucleotide sequence encoding a psoriastatin type I or psoriastatin type II polypeptide, and/or equivalents of such nucleic acids. The term "nucleic acid", as used herein, can include fragments and equivalents. The term "equivalent" refers to nucleotide sequences encoding functionally equivalent polypeptides or functionally equivalent polypeptides which, for example, retain the ability to react with an antibody specific for a psoriastatin type I or psoriastatin type II polypeptide. Equivalent nucleotide sequences will include sequences that differ by one or more nucleotide substitutions, additions or deletions, such as allelic variants, and will, therefore, include sequences that differ from the nucleotide sequence of psoriastatin shown in SEQ ID NO:1 or SEQ ID NO:3 due to the degeneracy of the genetic code.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., New York); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

The psoriatatin type I and psoriastatin type II genes and polypeptides of the present invention are useful for studying, diagnosing and/or treating diseases associated with unwanted cell proliferation or less than desired levels of apoptosis. e.g., psoriasis. The gene (or fragment thereof) can be used to prepare antisense constructs capable of inhibiting expression of a mutant or wild type psoriastatin type I or II gene encoding a polypeptide having an undesirable function. Alternatively, a psoriastatin type I or II polypeptide can be used to raise antibodies capable of detecting proteins or protein levels associated with psoriasis. An antagonist of psoriastatin type I or II can be administered to a patient afflicted with psoriasis to inhibit the activity of a wild type psoriastatin type I or II polypeptide. Furthermore, psoriastatin type I or II peptides, antibodies or nucleic acids, can be used to identify psoriatic tissue. Because psoriastatin peptides localize to the nucleus, they can be used to deliver compounds to the nucleus. Anti-psoriastatin antibodies can be used to identify the nucleus.

Other features and advantages of the invention will be apparent from the following detailed description, and from the claims.

BRIEF DESCRIPTION OF THE FIGURES

FIG. 1A: Effect on lysosomal cysteine proteinases, cathepsin B (-s-), cathepsin H (-n-) and cathepsin L (-l-). FIG. 1B: Effect on plant cysteine proteinases, papain (-m-), ficin (-o-) and bromelain (-_-). The molar ratio between psoriastatin and enzymes ([I]/[E]) is shown in the abscissa. Residual enzyme activity was measured after preincubation with psoriastatin.

FIG. 3 is a listing of nucleotides 22 to 1194 of SEQ ID NO:1.

FIG. 4 is a listing of the amino acid sequence of SEQ ID NO:2.

FIG. 5 is a listing of the nucleic acid sequence of SEQ ID NO:3.

FIG. 6 is a listing of the amino acid sequence of SEQ ID NO:4.

DETAILED DESCRIPTION OF THE INVENTION

Purification of Psoriastatin

The final preparation obtained from Superose 12 gel chromatography demonstrated a single protein band with a Mr 43,000 in both reduced and non-reduced conditions by SDS PAGE. The molecular weight of psoriastatin was clearly distinguished from the epidermal cystatin and from LMW kininogen. Purification steps are summarized in Table 1. The specific activity increased 80-fold and the yield was 3.9%. The increase in specific activity and the yield were relatively low, however, due to the cystatin content in the crude extract. Sephacryl S-200 gel chromatography clearly separated psoriastatin from cystatin. Of the total papain inhibitor activity in the crude extract, it was calculated that approximately 40% of inhibition was resulted from psoriastatin and 60% from cystatin.

The purification protocol was essentially as follows. Psoriastatin was purified from psoriatic scale extract by Sephacryl S-200, DEAE Sepharose, high performance cation exchange Mono S, chromatofocusing Mono P and Superose 12 gel chromatographies.

This purification protocol may result in a mixture of psoriastatin type I and type II. Pure preparations of psoriastatin type I or type II can be produced recombinantly or by immunoaffinity methods which use antibodies which can distinguish between psoriasttin type I and type II.

TABLE 1

Summary of Psoriastatin Purification

| Purification Step | Volume (ml) | Protein (mg) | Total Activity (U) | Specific Activity (U/mg) | (%) | Yield |
|---|---|---|---|---|---|---|
| TBS Extract | 180.0 | 1296.0 | 1978 | 1.53 | 100.0 | |
| Sephacryl S-200 | 54.0 | 28.0 | 766 | 27.36 | 38.7 | |
| DEAE Sepharose | 2.5 | 6.3 | 409 | 64.92 | 20.7 | |
| Mono S | 1.1 | 2.77 | 234 | 84.48 | 11.8 | |
| Mono P | 0.7 | 1.27 | 114 | 89.76 | 6.4 | |
| Superose 12 | 0.7 | 0.57 | 70 | 122.81 | 3.5 | |

Purification of Cathepsins

Bovine cathepsin B, H and L were purified from fresh bovine kidney using the method of Dolene et al. (Biol. Chem. Hoppe-Seyler 373: 407–412 [1992]).

Production of Antibodies

Antibodies against the psoriastatin preparation were raised in rabbits by the injection of 0.5 mg of the purified psoriastatin in Freund's complete adjuvant followed by three booster shots in incomplete adjuvant IgG function was purified by protein A-Sepharose chromatography.

Inhibitor Assays: Effect on Cysteine Proteinases and Serine Proteinases

Figure 1A:
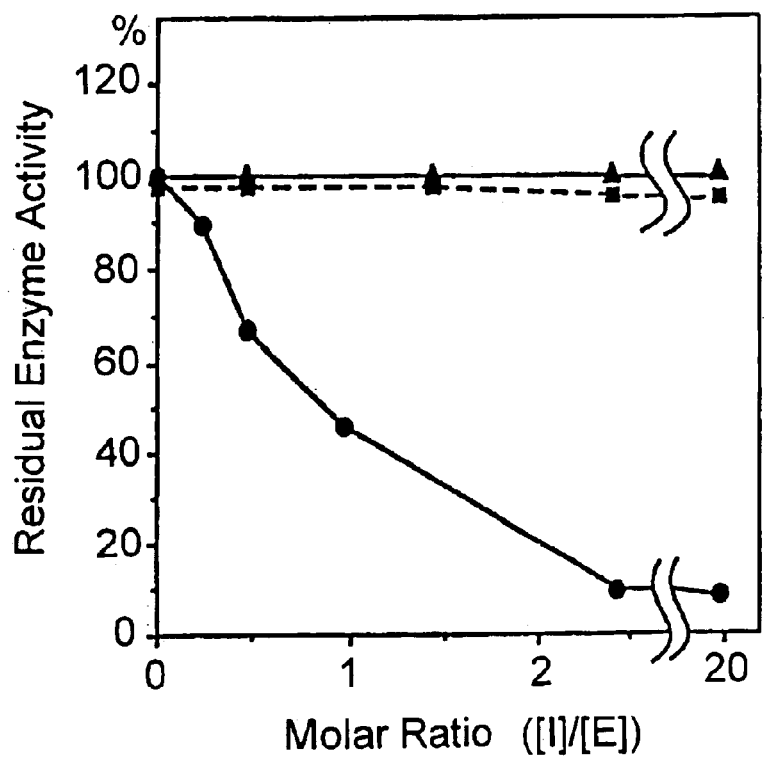
FIGS. 1A and 1B are graphs representing inhibition profiles of psoriastatin preparation on cysteine proteinases.
Figure 1B:
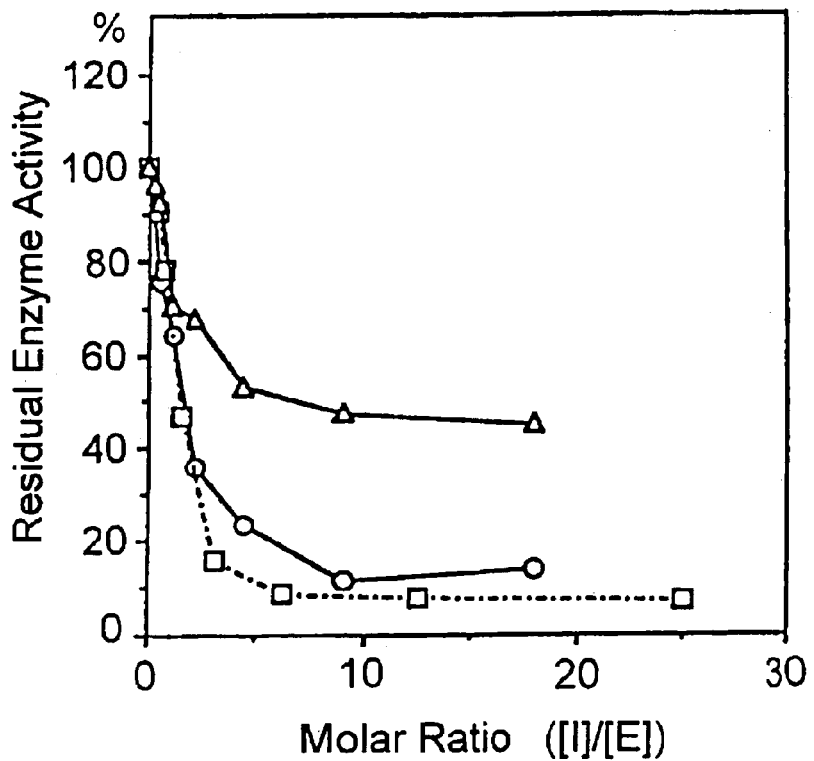

FIG. 1A demonstrates the effect of the psoriastatin preparation on lysosomal cysteine proteinases. Psoriastatin preparation inhibited cathepsin L in a dose dependent manner. It did not show any inhibitory effect on cathepsin B or H even at the concentration of 20 times molar excess of the inhibitor. It was conclude that the psoriastatin is a specific cathepsin L inhibitor. Inhibition profiles against plant cysteine proteinases are shown in FIG. 1B. Psoriastatin inactivated papain, ficin and bromelain, although the inhibition of bromelain was somewhat weak compared to that of papain and ficin. Ki values of psoriastatin for cathepsin L and papain were calculated as 1.9 nM and 1.68 nM, respectively. These values reveal the formation of tightly bound complexes with these enzymes.

Figure 2:
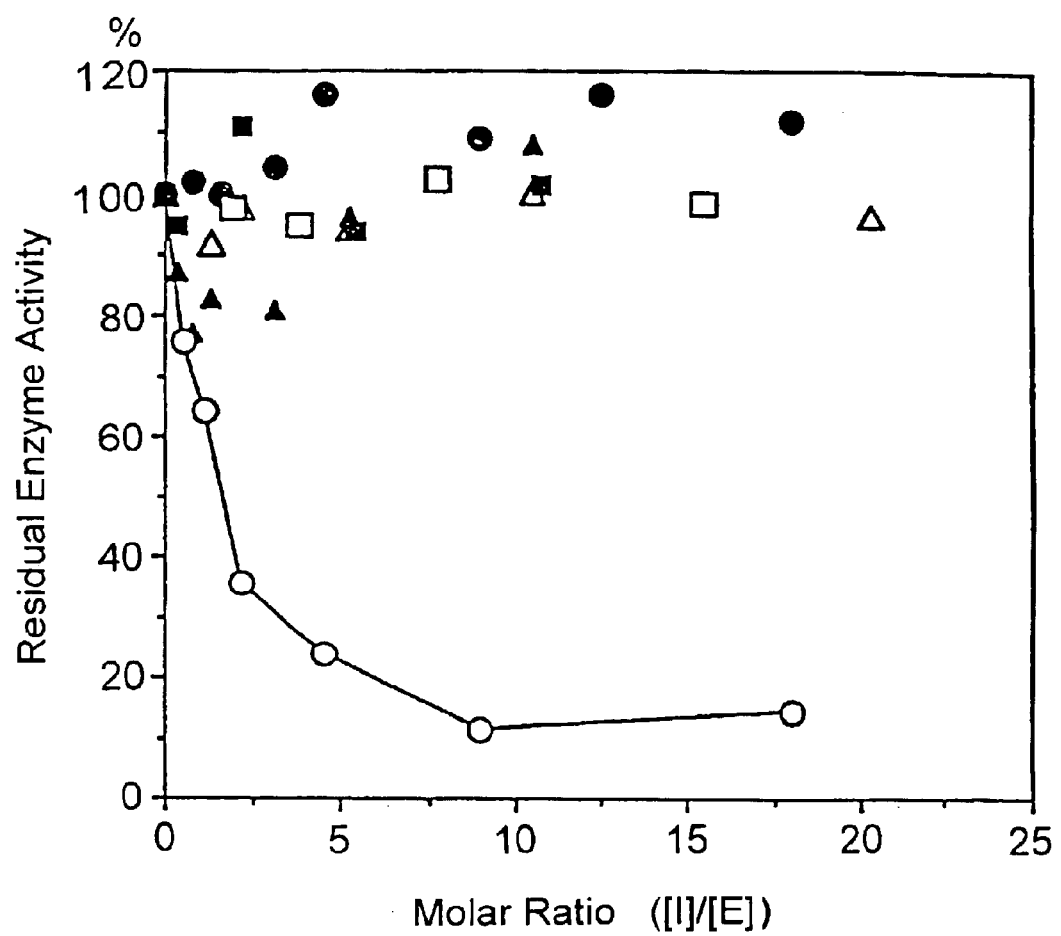
FIG. 2 is a graph depicting the effect of psoriastatin preparation on serine proteinases. Urokinase (o), plasmin (s), thrombin (_), chymotrypsin (n), or trypsin (1) was incubated with psoriastatin (up to 20 times molar excess) and residual enzyme activity was measured. Inhibition on papain (-m-) was also shown.

Since the homology search clearly demonstrated the similarity of psoriastatin with serpins, we tested its inhibitory effects on serine proteinases. As shown in FIG. 2, psoriastatin did not show any inhibitory effect on urokinase, plasmin, thrombin, chymotrypsin or trypsin, confirming that psoriastatin should be considered as a new member of cysteine proteinase inhibitor, although it showed a strong homology to serpins.

The inhibition assays were performed essentially as follows. Cathepsin L activity was determined using Z-Phe-Arg-MCA as a substrate (Barrett and Kirschke (1981) *Methods Enzymol,* 80:535–561). The ability of psoriastatin to inhibit cathepsin L was determined by incubating the inhibitor with cathepsin L for 10 min prior to the addition of the substrate. Ki values for cathepsin L and papain were calculated from the intersection of Dixon plots (correlation between [I] and 1/V) obtained at different substrate concentrations. BANA was usd as a substrate for the inhibition against papain, ficin and bromelain (Ito et al. (1984) *J. Invest. Dermatol* 83, 265–269). Inhibition for serine proteinases were assayed using chromogenic substrates (Hibino et al. (1986) *FEBS Lett.* 208: 273–277).

Electrophoresis and Immunoblotting

Homogeneity and molecular weight of the psoriastatin preparation was determined by SDS-polyacrylamide gel electrophoresis (PAGE) (Laemrnli, U.K. (1970) *Nature* 227: 680–685). Interaction between psoriastatin and cathepsin L at different pHs was also investigated using SDS-PAGE, followed by immunoblot analysis. Equimolar mixtures of the inhibitor and cathepsin L at pH 5.0, and 6.5 were kept at room temperature up to 150 min. The reaction was terminated by adding 0.25 volume of SDS-PAGE sample buffer (Hibino et al. (1986) *FEBS Lett.* 208:273–277) and boiling for 3 min. Proteins separated by SDS-PAGE were electrically transferred onto the PVDF membrane (Millipore, Mass.). The membrane was incubated with the rabbit anti-psoriastatin IgG, and then reacted with alkaline phosphatase-conjugated anti-rabbit IgG (Promega, Madison, Wis.). Nitro blue tetrazolium and 5-bromo-4-chloro-3-indolyl-phosphate (Promega) were used for color development.

Amino Acid Sequence Analysis of Tryptic Fragments

Sequence data were obtained from the tryptic peptides of psoriastatin. One hundred eighty-six residues were successfully sequenced, which covers nearly one half of the molecular weight of psoriastatin.

The sequencing experiments were essentially performed as follows. Approximately 100 mg of the purified psoriastatin were digested with 1 mg of trypsin at 37° C. for 6 hours and generated fragments were separated by reverse phase HPLC using TSK Phenyl 5PW RP column (Toso, Japan). Among the 36 major peaks isolated, 19 peptides were sequenced with an Applied Biosystem 470 A gas-phase Sequenator.

Cloning and characterization of psoriastatin type I and psoriastatin type II

Approximately 4 mg of poly(A)+ RNA was isolated from psoriatic skin through shave biopsy. A psoriasis cDNA library was constructed using the lZAP Express cDNA Synthesis Kit (Stratagene). cDNAs of around 2,000 bp were inserted into the ZAP Express vector and packaged with the Gigapack II Gold packaging extract (Stratagene). The library was screened with a cDNA fragment obtained by PCR using primers that were based on the sequence of a tryptic peptide. After the tertiary screening, 25 positive clones were isolated and analyzed. None of the clones contained 5' end sequences. Full length clones were obtained using the 5' RACE system (GIBCO). Restriction enzyme analysis of these clones using Pst I digestion demonstrated two distinct groups of psoriastatin cDNAs. One of the clones was sequenced and found to contain a sequence highly homologous to SCC-A from nucleotides 896 to 1711 with nucleotide 1130G replaced by A in psoriastatin type I gene. The G to A substitution at position 1130 along with 5 other substitutions (as compared to SCC-A) was confirmed by sequencing the TA clones constructed from different sources. The G to A substitution at position 1130 causes an amino acid change from Ala to Thr at position 357, which may correspond to the P'2 or P'3 position of reactive site of homologous serpins. The open reading frame of the novel gene, psoriastatin type I, is 390 amino acids in length Differences of Ki values of Cathepsin L between psoriastin preparation (5.9 nM) and SCC-A (0.067 nM could be explained by this amino acid substitution.

Several of the clones sequenced contained a sequence distinct from the psoriastatin type I gene. This sequence was named psoriastatin type II gene because of its high homology to psoriastatin type I gene. The open reading frame of the novel gene, psoriastatin type II, is 390 amino acids in length. This clone, at amino acid residues 351–357 (corresponding to amino acid residues 351–357 of SCC-A), varies greatly from the reactive site of homologous serpins. The clone is about 40% homologous to the crmA gene that is known to be involved in inhibition of ICE-like enzyme involved in regulation of apoptosis.

Alignment analysis of the predicted proteins using the GCG program revealed that psoriastatin type I and type II were 98% and 91% homologous with SCC-A, respectively. Both tppes were subcloned into pGEX-4T-2 vector and expressed as GST-fusion proteins. Only psoriastatin type I showed inhibitor activity against chatepsin L, demonstrating a functional difference between type I and type II psoriastatin.

Psoriastatin Expression Studies

The preliminary studies have revealed that heavy staining of psoriastatin, using antibody raised against the psoriastatin mixture described above, is always found in all cases of psoriasis examined (10/10), whereas it is only weakly positive in a low number (2/8) of squamous cell carcinoma (SCC). The presence of this molecule, therefore, is clearly an indicator for psoriasis and not for SCC. The name psoriastatin was given to this inhibitor, since this inhibitor is not found in normal epidermal extract and all the psoriasis patient tested (n=15) demonstrated the presence of this particular inhibitor.

Immuno Electron Microscopy

An antibody raised against the psoriastatin mixture described above was used to localiz psoriastatin in psoriatic epidermis using electron microscopy. The results indicate that psoriastatin localizes in the nucleus of the cell, as well as in the cytoplasm, and cell—cell contac area. An antibody raised against psoriastatin type I failed to localize this protein to the nucleus Other Procedures Which Can Be Used to Practice the Invention Gene Therapy The gene constructs of the invention can also be used as a part of a gene therapy protocol to deliver nucleic acids encoding either an agonistic or antagonistic form of a psoriastatin type I or II polypeptide. The invention features expression vectors for in vivo transfection and expression of a psoriastatin type I or II polypeptide in particular cell types (e.g., dermal cells) so as to reconstitute the function of, enhance the function of, or alternatively, antagonize the function of a psoriastatin type I or II polypeptide in a cell in which the polypeptide is expressed or misexpressed.

Expression constructs of psoriastatin type I or II polypeptides, may be administered in any biologically effective carrier, e.g. any formulation or composition capable of effectively delivering the psoriastatin type I or II gene to cells in vivo. Approaches include insertion of the subject gene into viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, granacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA encoding a psoriastatin type I or II polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retrovinises and for infecting cells in vitro or in vivo with such viruses can be found in *Current Protocols in Molecular Biology* Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol* 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenoviuss can be manipulated such that it encodes and expresses a gene product of interest but is inactivated in terms of its ability to replicate in a normal lytic viral life cycle. See, for example, Berlcner et al. (1988) *BioTechniques* 6:616; Rosenfeld et al. (1991) *Science* 252:431434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject psoriastatin type I or II gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of a psoriastatin type I or II polypeptide in the tissue of a mammal, such as a human. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject psoriastatin type I or II gene by the targeted cell. Exemplary gene delivery systems of this type include liposomal derived systems, poly-lysine conjugates, and artificial viral envelopes.

In a representative embodiment, a gene encoding a psoriastatin type I or II polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic psoriastatin type I or II gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. 5,328,470) or by stereotactic injection (e.g. Chen et al. (1994) *PNAS* 91: 3054–3057). In a preferred embodiment of the invention, the psoriastatin type I or II gene is targeted to dermal cells.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Antisense Therapy

Another aspect of the invention relates to the use of the isolated nucleic acid in "antisense" therapy. As used herein, "antisense" therapy refers to administration or in situ generation of oligonucleotides or their derivatives which specifically hybridize (e.g. bind) under cellular conditions, with the cellular mRNA and/or genomic DNA encoding a psoriastatin type I or II polypeptide, or mutant thereof, so as to inhibit expression of the encoded protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

In one embodiment, the antisense construct binds to a naturally-occurring sequence of a psoriastatin type I or II gene which, for example, is involved in expression of the gene. These sequences include, for example, start codons, stop codons, and RNA primer binding sites.

In another embodiment, the antisense construct binds to a nucleotide sequence which is not present in the wild type gene. For example, the antisense construct can bind to a region of apsoriastatin type I or II gene which contains an insertion of an exogenous, non-wild type sequence. Alternatively, the antisense construct can bind to a region of a psoriastatin type I or II gene which has undergone a deletion, thereby bringing two regions of the gene together which are not normally positioned together and which, together, create a non-wild type sequence.

When administered in vivo to a subject, antisense constructs which bind to non-wild type sequences provide the advantage of inhibiting the expression of mutant psoriastatin type I or II gene, without inhibiting expression of any wild type psoriastatin type I or II gene.

An antisense construct of the present invention can be delivered, for example, as an expression plasmid which, when transcribed in the cell, produces RNA which is complementary to at least a unique portion of the cellular mRNA which encodes a psoriastatin type I or II polypeptide. Alternatively, the antisense construct is an oligonucleotide probe which is generated ex vivo and which, when introduced into the cell causes inhibition of expression by hybridizing with the mRNA and/or genomic sequences of a psoriastatin type I or II gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Accordingly, the modified oligomers of the invention are useful in therapeutical diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included in the invention.

The compounds can be administered orally or by transmucosal or transdermal means. For transmucosal or transdermal administration, penetrants appropriate to the barrier to be permeated are used in the formulation. Such penetrants are known in the art and include, for example, for transmucosal administration bile salts and fusidic acid derivatives, and detergents. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as known in the art.

In addition to use in therapy, the oligomers of the invention may be used as diagnostic reagents to detect the presence or absence of the target DNA or RNA sequences to which they specifically bind.

The antisense constructs of the present invention, by antagonizing the expression of a psoriastatin type I or II gene, can be used in the manipulation of tissue, both in vivo and in ex vivo tissue cultures.

Transgenic Animals

The invention includes transgenic animals which include cells (of that animal) which contain a psoriastatin type I and/or II transgene and which preferably (though optionally) express (or misexpress) an endogenous or exogenous psoriastatin type I and/or II gene in one or more cells in the animal.

The psoriastatin type I and/or II transgene can encode a mutant psoriastatin type I and/or II polypeptide. Such animals can be used as disease models or can be used to screen for agents effective at correcting the misexpression of psoriastatin type I and/or II. Alternatively, the psoriastatin type I and/or II transgene can encode the wild-type forms of the protein, or can encode homologs thereof, including both agonists and antagonists, as well as antisense constructs. In preferred embodiments, the expression of the tansgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns. Temporal patterns of expression can be provided by, for example, conditional recombination systems or prokaryotic transcriptional regulatory sequences. In preferred embodiments, the transgenic animal carries a "knockout" psoriastatin type I and/or II gene, i.e., a deletion of all or a part of either genes or both genes ("double knockout").

Genetic techniques which allow for the expression of transgenes, that are regulated in vivo via site-specific genetic manipulation, are known to those skilled in the art. For example, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject psoriastatin type I and/or II gene. For example, excision of a target sequence which interferes with the expression of a recombinant psoriastatin type I and/or II gene, such as one which encodes an agonistic homolog, can be designed to activate expression of that gene. This interference with expression of the protein can result from a variety of mechanisms, such as spatial separation of the psoriastatin type I and/or II gene from the promoter element or an internal stop codon.

Moreover, the transgene can be made so that the coding sequence of the gene is flanked with recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation. See e.g., descriptions of the cre/loxP recombinase system of bacteriophage P1 (Lakso et al. (1992) *PNAS* 89:6232–6236; Orban et al. (1992) PNAS 89:6861–6865) or the FLP recombinase system of *Saccharonyces cerevisiae* (O'Gorman et al. (1991) *Science* 251:1351–1355; PCT publication WO 92/15694). Genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element Thus, the activation expression of the recombinant psoriastatin type I and/or II gene can be regulated via control of recombinase expression.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the psoriastatin type I and/or II transgene could remain silent into adulthood until "turned on" by the introduction of the trans-activator.

Production of Fragments and Analogs

The inventor has provided the primary amino acid structure of a psoriastatin type I and a psoriastatin type II polypeptides. Once an example of this core structure has been provided, one skilled in the art can alter the disclosed structure by producing fragments or analogs, and testing the newly produced structures for activity. Examples of prior art methods which allow the production and testing of fragments and analogs are discussed below. These, or analogous methods can be used to make and screen fragments and analogs of a psoriastatin type I or II polypeptide having at least one biological activity e.g., which react with an antibody (e.g., a monoclonal antibody) specific for a psoriastatin type I or II polypeptide.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Production of Altered DNA and Peptide Sequences: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (eung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complementary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Production of Altered DNA and Peotide Sequences: Methods for Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alacine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (DNA 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA Generally, oligonucleotides of at least 25 nucleotides in length are used An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765[1978]). For purposes of the present invention, preferred oligonucleotide primers have a nucleotide sequence shown in SEQ ID NOS: 3–15.

Cassette Mutagenesis

Another method for preparing variants, cassette mutagenesis, is based on the technique described by Wells et al. (*Gene*, 34:315 [1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants, e.g., a library of variants which is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Petptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to an antibody specific for a psoriastatin type I or II polypeptide. Each of the techniques described below is amenable to high through-put analysis for screening large numbers of sequences created, e.g., by random mutagenesis techniques.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370–1371; and Goward et al. (1992) TIBS 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol Chem. 267:16007–16010; Griffiths et al. (1993) EMBOJ 12:725–734; Clackson et al. (1991) Nature 352:624–628; and Barbas et al. (1992) PNAS 89:4457–4461).

A common approach uses the maltose receptor of E. coli (the outer membrane protein, LamB) as a peptide fusion partner (Charbit et al. (1986) EMBO 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) Vaccines 91, pp. 387–392), PhoE (Agterberg, et al. (1990) Gene 88, 37–45), and PAL (Fuchs et al. (1991) Bio/Tech 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells Kuwajima et al. (1988) Bio/Tech. 6, 1080–1083). Surface proteins of other bacterial species have also served as peptide fusion partners. Examples include the Staphylococcus protein A and the outer membrane protease IgA of Neisseria (Hansson et al. (1992) J. Bacteriol. 174, 4239–4245 and Klauser et al. (1990) EMBO J. 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) PNAS USA 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) Proc. Natl. Acad. Sci. U.S.A. 89-1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) Proc. Natl. Acad. Sci. U.S.A. 87, 6378–6382) A second difference is the set of biological biases affecting the population of peptides actually present in the libraries. The Lacd fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the Lad and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are under represented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/ phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–125 1), a molecular DNA library encoding $10^{12}$ decapeptides was constructed and the library expressed in an *E. coli* S30 in vitro coupled transcription/ translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of a protein of interest is identified, such as the primary amino acid sequence of psoriastatin type I and II polypeptides as disclosed herein, it is routine to perform for one skilled in the art to obtain analogs and fragments.

Antibodies

The invention also includes antibodies specifically reactive with a subject psoriastatin type I or II polypeptide. Anti-protein/anti-peptide antisera or monoclonal antibodies can be made by standard protocols (See, for example, *Antibodies: A Laboratory Manual ed*, by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject psoriastatin type I or II polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the psoriastatin type I or II polypeptide of the invention, e.g. antigenic determinants of a polypeptide of SEQ ID NO:2 or SEQ ID NO:4.

The term "antibody", as used herein, intended to include fragments thereof which are also specifically reactive with a psoriastatin type I or II polypeptide. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments.

Both monoclonal and polyclonal antibodies (Ab) directed against psoriastatin type I or II polypeptides, or fragments or analogs thereof, and antibody fragments such as Fab' and $F(ab')_2$, can be used to block the action of a psoriastatin type I or II polypeptide and allow the study of the role of a psoriastatin type I or II polypeptide of the present invention.

Antibodies which specifically bind psoriastatin type I or II polypeptide epitopes can also be used in immunohistochemical staining of tissue samples in order to evaluate the abundance and pattern of expression of psoriastatin type I or II polypeptide. Anti-psoriastatin type I or II polypeptide antibodies can be used diagnostically in immunoprecipitation and immuno-blotting to detect and evaluate wild type or mutant psoriastatin type I or II polypeptide levels in tissue or bodily fluid as part of a clinical testing procedure. Likewise, the ability to monitor psoriastatin type I or II polypeptide levels in an individual can allow determination of the efficacy of a given treatment regimen for an individual afflicted with disorders associated with modulation of apoptosis, e.g., psoriasis. The level of a psoriastatin type I or II polypeptide can be measured in tissue, such as produced by biopsy.

Another application of anti-psoriastatin type I or II antibodies of the present invention is in the immunological screening of cDNA libraries constructed in expression vectors such as lgt11, lgt18–23, lZAP, and lORF8. Messenger libraries of this type, having coding sequences inserted in the correct reading frame and orientation, can produce fusion proteins. For instance, lgt11 will produce fusion proteins whose amino termini consist of β-galactosidase amino acid sequences and whose carboxy termini consist of a foreign polypeptide. Antigenic epitopes of a subject psoriastatin type I or II polypeptide can then be detected with antibodies, as, for example, reacting nitrocellulose filters lifted from infected plates with anti-psoriastatin type I or II polypeptide antibodies. Phage, scored by this assay, can then be isolated from the infected plate. Thus, the presence of psoriastatin type I or II homologs can be detected and cloned from other animals, and alternate isoforms (including splicing variants) can be detected and cloned from human sources.

Drug Screening Assays

By making available purified and recombinant-psoriastatin type I or II polypeptides, the present invention provides assays which can be used to screen for drugs which are either agonists or antagonists of the normal cellular function, in this case, of the subject psoriastatin type I or II polypeptide. In one embodiment, the assay evaluates the ability of a compound to modulate binding between a psoriastatin type I or II polypeptide and a naturally occurring ligand, e.g., an antibody specific for a psoriastatin type I or II polypeptide. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target.

Other Embodiments

Included in the invention are: allelic variations; natural mutants; induced mutants; proteins encoded by DNA that hybridizes under high or low stringency conditions to a nucleic acids which encode polypeptides of SEQ ID NO:2 and SEQ ID NO:4. High stringency conditions for aqueous hybridization can be conducted at 65° C., using the high stringency wash buffer, 1 mM Na$_2$EDTA; 40 mM NaHPO$_4$, pH 7.2; and 1% SDS, and include multiple quick washes (5–8) and a final wash for 20 minutes (see Current Protocols in Molecular Biology, John Wiley & Sons, New York, 1989, 6.3.1–6.3.6); and, polypeptides specifically bound by antisera to a psoriastatin type I or II polypeptide.

The invention also includes fragments, preferably biologically active fragments, or analogs of a psoriastatin type I and II polypeptides. A biologically active fragment or analog is one having any in vivo or in vitro activity which is characteristic of the psoriastatin type I or II polypeptide shown in SEQ ID NO:2 or SEQ ID NO:4, or of other naturally occurring psoriastatin type I or II polypeptides, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Because peptides, such as a psoriastatin type I or II polypeptide, often exhibit a range of physiological properties and because such properties may be attributable to different portions of the molecule, a useful psoriastatin type I or II polypeptide fragment or psoriastatin type I or II polypeptide analog is one which exhibits a biological activity in any biological assay for psoriastatin type I or II polypeptide activity. Most preferably the fragment or analog possesses 10%, preferably 40%, or at least 90% of the activity of a psoriastatin type I or II polypeptide (SEQ ID NO:2 or SEQ ID NO:4), in any in vivo or in vitro psoriastatin type I or II polypeptide activity assay.

Analogs can differ from a naturally occurring psoriastatin type I or II polypeptide in amino acid sequence or in ways that do not involve sequence, or both. Non-sequence modifications include in vivo or in vitro chemical derivation of a psoriastatin type I or II polypeptide. Non-sequence modifications include changes in acetylation, methylation, phosphorylation, carboxylation, or glycosylation.

Preferred analogs include a psoriastatin type I or II polypeptide (or biologically active fragments thereof) whose sequences differ from the wild-type sequence by one or more conservative amino acid substitutions or by one or more non-conservative amino acid substitutions, deletions, or insertions which do not abolish the Issoriastatin type I or II polypeptide biological activity. Conservative substitutions typically include the substitution of one amino acid for another with similar cathartics, e.g., substitutions within the following groups: valine, glycine; glycine, alanine; valie, isoleucine, leucine; aspartic acid, glutanc acid; asparagine, gluaie; serine, thenine; lysine, arginine; and phenylalame, tyrosmne. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidane-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to a psoriastatin type I or II polypeptide analog, will ordinarily be at least about 20 residues, more typically at least about 40 residues, preferably at least about 60 residues in length. Fragments of a psoriastatin type I or II polypeptide can be generated by methods known to those skilled in the art. The ability of a candidate fragment to exhioit a biological activity of a psoriastatin type I or II polypeptide can be assessed by methods known to those skilled in the art, as described herein. Also included are psoriastatin type I and II polypeptides containing residues that are not required for biological activity of the peptide or that result from alternative mRNA splicing or alternative protein processing events.

In order to obtain a psoriastatin type I or II polypeptide, a psoriastatin type I or II polypeptide-encoding DNA can be introduced into an expression vector, the vector introduced into a cell suitable for expression of the desired protein, and the peptide recovered and purified, by prior art methods. Antibodies to the peptides an proteins can be made by immunizing an animal, e.g., a rabbit or mouse, and recovering anti-psoriastatin type I or II polypeptide antibodies by prior art methods.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A method of promoting apoptosis, comprising administering an antibody that inhibits a psoriastatin-1, wherein the psoriastatin-1 comprises the amino acid sequence of SEQ ID NO:2.

2. The method of claim 1, wherein the antibody is a monoclonal antibody.

3. The method of claim 1, wherein the antibody is a polyclonal antibody.

4. The method of claim 1, wherein the antibody is administered to a mammal.

5. The method of claim 1, wherein the antibody is administered to a primate.

6. The method of claim 1, wherein the antibody is administered to a human.

7. The method of claim 1, wherein the antibody is administered to a rodent.

8. The method of claim 1, wherein the antibody is administered to a mouse.

9. The method of claim 1, wherein the antibody is administered to a rat.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1193 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 22..1193

(xi) SEQUENCE DESCRIPTION: SEQ ID NO:1:

```
CCAGATCACA TCGAGTTCAC C ATG AAT TCA CTC AGT GAA GCC AAC ACC AAG         51
                         Met Asn Ser Leu Ser Glu Ala Asn Thr Lys
                          1               5                  10

TTC ATG TTC GAC CTG TTC CAA CAG TTC AGA AAA TCA AAA GAG AAC AAC          99
Phe Met Phe Asp Leu Phe Gln Gln Phe Arg Lys Ser Lys Glu Asn Asn
            15                  20                  25

ATC TTC TAT TCC CCT ATC AGC ATC ACA TCA GCA TTA GGG ATG GTC CTC         147
Ile Phe Tyr Ser Pro Ile Ser Ile Thr Ser Ala Leu Gly Met Val Leu
                30                  35                  40

TTA GGA GCC AAA GGC AAC ACT GCA CAA CAG ATT AAG AAG GTT CTT CAC         195
Leu Gly Ala Lys Gly Asn Thr Ala Gln Gln Ile Lys Lys Val Leu His
            45                  50                  55

TTT GAT CAA GTC ACA GAG AAC ACC ACA GGA AAA GCT GCA ACA TAT CAT         243
Phe Asp Gln Val Thr Glu Asn Thr Thr Gly Lys Ala Ala Thr Tyr His
        60                  65                  70

GTT GAT AGG TCA GGA GAT GTT CAT CAC CAG TTT CAA AAG CTT CTG ACT         291
Val Asp Arg Ser Gly Asp Val His His Gln Phe Gln Lys Leu Leu Thr
75                  80                  85                  90

GAA TTC AAC AAA TCC ACT GAT GCA TAT GAG CTG AAG ATC GCC AAC AAG         339
Glu Phe Asn Lys Ser Thr Asp Ala Tyr Glu Leu Lys Ile Ala Asn Lys
                95                 100                 105

CTC TTC GGA GAA AAA ACG TAT CTA TTT TTA CAG GAA TAT TTA GAT GCC         387
Leu Phe Gly Glu Lys Thr Tyr Leu Phe Leu Gln Glu Tyr Leu Asp Ala
            110                 115                 120
```

```
ATC AAG AAA TTT TAC CAG ACC AGT GTG GAA TCT GTT GAT TTT GCA AAT      435
Ile Lys Lys Phe Tyr Gln Thr Ser Val Glu Ser Val Asp Phe Ala Asn
        125                 130                 135

GCT CCA GAA GAA AGT CGA AAG AAG ATT AAC TCC TGG GTG GAA AGT CAA      483
Ala Pro Glu Glu Ser Arg Lys Lys Ile Asn Ser Trp Val Glu Ser Gln
    140                 145                 150

ACG AAT GAA AAA ATT AAA AAC CTA ATT CCT GAA GGT AAT ATT GGC AGC      531
Thr Asn Glu Lys Ile Lys Asn Leu Ile Pro Glu Gly Asn Ile Gly Ser
155                 160                 165                 170

AAT ACC ACA TTG GTT CTT GTG AAC GCA ATC TAT TTC AAA GGG CAG TGG      579
Asn Thr Thr Leu Val Leu Val Asn Ala Ile Tyr Phe Lys Gly Gln Trp
                175                 180                 185

GAG AAG AAA TTT AAT AAA GAA GAT ACT AAA GAG GAA AAA TTT TGG CCA      627
Glu Lys Lys Phe Asn Lys Glu Asp Thr Lys Glu Glu Lys Phe Trp Pro
            190                 195                 200

AAC AAG AAT ACA TAC AAG TCC ATA CAG ATG ATG AGG CAA TAC ACA TCT      675
Asn Lys Asn Thr Tyr Lys Ser Ile Gln Met Met Arg Gln Tyr Thr Ser
        205                 210                 215

TTT CAT TTT GCC TCG CTG GAG GAT GTA CAG GCC AAG GTC CTG GAA ATA      723
Phe His Phe Ala Ser Leu Glu Asp Val Gln Ala Lys Val Leu Glu Ile
220                 225                 230

CCA TAC AAA GGC AAA GAT CTA AGC ATG ATT GTG TTG CTG CCA AAT GAA      771
Pro Tyr Lys Gly Lys Asp Leu Ser Met Ile Val Leu Leu Pro Asn Glu
235                 240                 245                 250

ATC GAT GGT CTC CAG AGG CTT GAA GAG GAA CTC ACT GCT GAG AAA TTG      819
Ile Asp Gly Leu Gln Arg Leu Glu Glu Glu Leu Thr Ala Glu Lys Leu
                255                 260                 265

ATG GAA TGG ACA AGT TTG CAG AAT ATG AGA GAG ACA CGT GTC GAT TTA      867
Met Glu Trp Thr Ser Leu Gln Asn Met Arg Glu Thr Arg Val Asp Leu
            270                 275                 280

CAC TTA CCT CGG TTC AAA GTG GAA GAG AGC TAT GAC CTC AAG GAC ACG      915
His Leu Pro Arg Phe Lys Val Glu Glu Ser Tyr Asp Leu Lys Asp Thr
        285                 290                 295

TTG AGA ACC ATG GGA ATG GTG GAT ATC TTC AAT GGG GAT GCA GAC CTC      963
Leu Arg Thr Met Gly Met Val Asp Ile Phe Asn Gly Asp Ala Asp Leu
300                 305                 310

TCA GGC ATG ACC GGG AGC CGC GGT CTC GTG CTA TCT GGA GTC CTG CAC     1011
Ser Gly Met Thr Gly Ser Arg Gly Leu Val Leu Ser Gly Val Leu His
315                 320                 325                 330

AAG GCC TTT GTG GAG GTT ACA GAG GAG GGA GCA GAA GCT GCA GCT GCC     1059
Lys Ala Phe Val Glu Val Thr Glu Glu Gly Ala Glu Ala Ala Ala Ala
                335                 340                 345

ACC GCT GTA GTA GGA TTC GGA TCA TCA CCT ACT TCA ACT AAT GAA GAG     1107
Thr Ala Val Val Gly Phe Gly Ser Ser Pro Thr Ser Thr Asn Glu Glu
            350                 355                 360

TTC CAT TGT AAT CAC CCT TTC CTA TTC TTC ATA AGG CAA AAT AAG ACC     1155
Phe His Cys Asn His Pro Phe Leu Phe Phe Ile Arg Gln Asn Lys Thr
        365                 370                 375

AAC AGC ATC CTC TTC TAT GGC AGA TTC TCA TCC CCG TA                  1193
Asn Ser Ile Leu Phe Tyr Gly Arg Phe Ser Ser Pro
380                 385                 390
```

(2) INFORMATION FOR SEQ ID NO:2:

(i) SEQUENCE CHARACTERISTICS:
        (A) LENGTH: 390 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Ser Leu Ser Glu Ala Asn Thr Lys Phe Met Phe Asp Leu Phe
 1               5                  10                  15

Gln Gln Phe Arg Lys Ser Lys Glu Asn Asn Ile Phe Tyr Ser Pro Ile
                20                  25                  30

Ser Ile Thr Ser Ala Leu Gly Met Val Leu Leu Gly Ala Lys Gly Asn
            35                  40                  45

Thr Ala Gln Gln Ile Lys Lys Val Leu His Phe Asp Gln Val Thr Glu
        50                  55                  60

Asn Thr Thr Gly Lys Ala Ala Thr Tyr His Val Asp Arg Ser Gly Asp
 65                  70                  75                  80

Val His His Gln Phe Gln Lys Leu Leu Thr Glu Phe Asn Lys Ser Thr
                85                  90                  95

Asp Ala Tyr Glu Leu Lys Ile Ala Asn Lys Leu Phe Gly Glu Lys Thr
                100                 105                 110

Tyr Leu Phe Leu Gln Glu Tyr Leu Asp Ala Ile Lys Lys Phe Tyr Gln
            115                 120                 125

Thr Ser Val Glu Ser Val Asp Phe Ala Asn Ala Pro Glu Glu Ser Arg
        130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
                165                 170                 175

Val Asn Ala Ile Tyr Phe Lys Gly Gln Trp Glu Lys Lys Phe Asn Lys
            180                 185                 190

Glu Asp Thr Lys Glu Glu Lys Phe Trp Pro Asn Lys Asn Thr Tyr Lys
        195                 200                 205

Ser Ile Gln Met Met Arg Gln Tyr Thr Ser Phe His Phe Ala Ser Leu
    210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Arg
                245                 250                 255

Leu Glu Glu Glu Leu Thr Ala Glu Lys Leu Met Glu Trp Thr Ser Leu
            260                 265                 270

Gln Asn Met Arg Glu Thr Arg Val Asp Leu His Leu Pro Arg Phe Lys
        275                 280                 285

Val Glu Glu Ser Tyr Asp Leu Lys Asp Thr Leu Arg Thr Met Gly Met
290                 295                 300

Val Asp Ile Phe Asn Gly Asp Ala Asp Leu Ser Gly Met Thr Gly Ser
305                 310                 315                 320

Arg Gly Leu Val Leu Ser Gly Val Leu His Lys Ala Phe Val Glu Val
                325                 330                 335

Thr Glu Glu Gly Ala Glu Ala Ala Ala Thr Ala Val Val Gly Phe
            340                 345                 350

Gly Ser Ser Pro Thr Ser Thr Asn Glu Glu Phe His Cys Asn His Pro
        355                 360                 365

Phe Leu Phe Phe Ile Arg Gln Asn Lys Thr Asn Ser Ile Leu Phe Tyr
    370                 375                 380

Gly Arg Phe Ser Ser Pro
385                 390
```

(2) INFORMATION FOR SEQ ID NO:3:

(i) SEQUENCE CHARACTERISTICS:
    (A) LENGTH: 953 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 3..950

(xi) SEQUENCE DESCRIPTION: SEQ ID NO:3:

```
TT GAT AGG TCA GGA AAT GTT CAT CAC CAG TTT CAA AAG CTT CTG ACT        47
   Asp Arg Ser Gly Asn Val His His Gln Phe Gln Lys Leu Leu Thr
   1               5                   10                  15

GAA TTC AAC AAA TCC ACT GAT GCA TAT GAG CTG AAG ATC GCC AAC AAG       95
Glu Phe Asn Lys Ser Thr Asp Ala Tyr Glu Leu Lys Ile Ala Asn Lys
                20                  25                  30

CTC TTC GGA GAA AAG ACG TNT CAA TTT TTA CAG GAA TAT TTA GAT GCC      143
Leu Phe Gly Glu Lys Thr Xaa Gln Phe Leu Gln Glu Tyr Leu Asp Ala
            35                  40                  45

ATC AAG AAA TTT TAC CAG ACC AGT GTG GAA TCT ACT GAT TTN GNA AAT      191
Ile Lys Lys Phe Tyr Gln Thr Ser Val Glu Ser Thr Asp Xaa Xaa Asn
        50                  55                  60

GCT CCA GAA GAA AGT CGA AAG AAG ATT AAC TCC TGG GTG GAA AGT CAA      239
Ala Pro Glu Glu Ser Arg Lys Lys Ile Asn Ser Trp Val Glu Ser Gln
65                  70                  75

ACG AAT GAA AAA ATT AAA AAC CTA TTT CCT GAT GGG ACT ATT GGC AAT      287
Thr Asn Glu Lys Ile Lys Asn Leu Phe Pro Asp Gly Thr Ile Gly Asn
80                  85                  90                  95

GAT ACG ACA CTG GTT CTT GTG AAC GCA ATC TAT TTC AAA GGG CAG TGG      335
Asp Thr Thr Leu Val Leu Val Asn Ala Ile Tyr Phe Lys Gly Gln Trp
                100                 105                 110

GAG AAT AAA TTT AAA AAA GAA AAC ACT AAA GAG GAA AAA TTT TGG CCA      383
Glu Asn Lys Phe Lys Lys Glu Asn Thr Lys Glu Glu Lys Phe Trp Xaa
            115                 120                 125

AAC AAG AAT ACA TAC AAA TCT GTA CAG ATG ATA AGG CAA TAC AAT TCC      431
Asn Lys Asn Thr Tyr Lys Ser Val Gln Met Ile Arg Gln Tyr Asn Ser
        130                 135                 140

TTT AAT TTT GCC TTG CTT GAG GAT GTA CAG GCC AAG GTC CTG GAA ATA      479
Phe Asn Phe Xaa Leu Leu Glu Asp Val Gln Ala Lys Val Leu Glu Ile
145                 150                 155

CCA TAC AAA GGC AAA GAT CTA AGC ATG ATT GTG CTG CTG CCA AAT GAA      527
Pro Tyr Lys Gly Lys Asp Leu Ser Met Ile Val Leu Leu Pro Asn Glu
160                 165                 170                 175

ATC GAT GGT CTG CAG AAG CTT GAA GAG AAA CTC ACT GCT GAG AAA TTG      575
Ile Asp Gly Leu Gln Lys Leu Glu Glu Lys Leu Thr Ala Glu Lys Leu
                180                 185                 190

ATG GAA TGG ACA AGT TTG CAG AAT ATG AGA GAG ACA TGT GTC GAT TTA      623
Met Glu Trp Thr Ser Leu Gln Asn Met Arg Glu Thr Cys Val Asp Leu
            195                 200                 205

CAC TTA CCT CGG TTC AAA ATG GAA GAG AGC TAT GAC CTC AAG GAC ACG      671
His Leu Pro Arg Phe Lys Met Glu Glu Ser Tyr Asp Leu Lys Asp Thr
        210                 215                 220

TTG AGA ACC ATG GGA ATG GTG AAT ATC TTC AAT GGG GAT GCA GAC CTC      719
Leu Arg Thr Met Gly Met Val Asn Ile Phe Asn Gly Asp Ala Asp Leu
225                 230                 235

TCA GGC ATG ACC TGG AGC CAC GGT CTC TCA GTA TCT AAA GTC CTA CAC      767
Ser Gly Met Thr Trp Ser His Gly Leu Ser Val Ser Lys Val Leu His
240                 245                 250                 255
```

-continued

```
AAG GCC TTT GTG GAG GTC ACT GAG GAG GGA GTG GAA GCT GCA GCT GCC       815
Lys Xaa Phe Val Glu Val Thr Glu Glu Gly Val Glu Ala Ala Ala Xaa
            260                 265                 270

ACC GCT GTA GTA GTA GTC GAA TTA TCA TCT CCT TCA ACT AAT GAA GAG       863
Thr Ala Val Val Val Val Glu Leu Ser Ser Pro Ser Thr Asn Glu Glu
                275                 280                 285

TTC TGT TGT AAT CAC CCT TTC CTA TTC TTC ATA AGG CAA AAT AAG ACC       911
Phe Cys Cys Asn His Pro Phe Leu Phe Phe Ile Arg Gln Asn Lys Thr
                    290                 295                 300

AAC AGC ATC CTC TTC TAT GGC AGA TTC TCA TCC CCG TAGATG                953
Asn Ser Ile Leu Phe Tyr Gly Arg Phe Ser Ser Pro
                        305                 310                 315
```

(2) INFORMATION FOR SEQ ID NO:4:

(i) SEQUENCE CHARACTERISTICS:
        (A) LENGTH: 315 amino acids
        (B) TYPE: amino acid
        (D) TOPOLOGY: linear (ii) MOLECULE TYPE: protein (xi) SEQUENCE DESCRIPTION: SEQ ID NO:4:

```
Asp Arg Ser Gly Asn Val His His Gln Phe Gln Lys Leu Leu Thr Glu
  1               5                  10                  15

Phe Asn Lys Ser Thr Asp Ala Tyr Glu Leu Lys Ile Ala Asn Lys Leu
             20                  25                  30

Phe Gly Glu Lys Thr Xaa Gln Phe Leu Gln Glu Tyr Leu Asp Ala Ile
         35                  40                  45

Lys Lys Phe Tyr Gln Thr Ser Val Glu Ser Thr Asp Xaa Xaa Asn Ala
 50                  55                  60

Pro Glu Glu Ser Arg Lys Lys Ile Asn Ser Trp Val Ser Gln Thr
 65                  70                  75                  80

Asn Glu Lys Ile Lys Asn Leu Phe Pro Asp Gly Thr Ile Gly Asn Asp
                 85                  90                  95

Thr Thr Leu Val Leu Val Asn Ala Ile Tyr Phe Lys Gly Gln Trp Glu
             100                 105                 110

Asn Lys Phe Lys Lys Glu Asn Thr Lys Glu Glu Lys Phe Trp Xaa Asn
         115                 120                 125

Lys Asn Thr Tyr Lys Ser Val Gln Met Ile Arg Gln Tyr Asn Ser Phe
130                 135                 140

Asn Phe Xaa Leu Leu Glu Asp Val Gln Ala Lys Val Leu Glu Ile Pro
145                 150                 155                 160

Tyr Lys Gly Lys Asp Leu Ser Met Ile Val Leu Leu Pro Asn Glu Ile
                 165                 170                 175

Asp Gly Leu Gln Lys Leu Glu Glu Lys Leu Thr Ala Glu Lys Leu Met
             180                 185                 190

Glu Trp Thr Ser Leu Gln Asn Met Arg Glu Thr Cys Val Asp Leu His
         195                 200                 205

Leu Pro Arg Phe Lys Met Glu Glu Ser Tyr Asp Leu Lys Asp Thr Leu
210                 215                 220

Arg Thr Met Gly Met Val Asn Ile Phe Asn Gly Asp Ala Asp Leu Ser
225                 230                 235                 240

Gly Met Thr Trp Ser His Gly Leu Ser Val Ser Lys Val Leu His Lys
                 245                 250                 255

Xaa Phe Val Glu Val Thr Glu Glu Gly Val Glu Ala Ala Ala Xaa Thr
             260                 265                 270
```

```
Ala Val Val Val Val Glu Leu Ser Ser Pro Ser Thr Asn Glu Glu Phe
        275                 280                 285

Cys Cys Asn His Pro Phe Leu Phe Phe Ile Arg Gln Asn Lys Thr Asn
    290                 295                 300

Ser Ile Leu Phe Tyr Gly Arg Phe Ser Ser Pro
305                 310             315

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:5:

Gly Phe Gly Ser Ser Pro Ala
1               5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:6:

Val Val Glu Leu Ser Ser Pro
1               5
```